United States Patent
Cui et al.

(10) Patent No.: US 11,517,234 B2
(45) Date of Patent: Dec. 6, 2022

(54) ELECTRODE SYSTEMS, DEVICES AND METHODS

(71) Applicant: University of Pittsburgh—Of the Commonwealth System of Higher Education, Pittsburgh, PA (US)

(72) Inventors: Xinyan Cui, Wexford, PA (US); Nicolas Alexander Alba, Pittsburgh, PA (US); Mingui Sun, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 1239 days.

(21) Appl. No.: 15/956,461

(22) Filed: Apr. 18, 2018

(65) Prior Publication Data

US 2018/0235492 A1 Aug. 23, 2018

Related U.S. Application Data

(62) Division of application No. 14/196,520, filed on Mar. 4, 2014, now Pat. No. 9,955,881, which is a division
(Continued)

(51) Int. Cl.
*A61B 5/24* (2021.01)
*A61N 1/04* (2006.01)
(Continued)

(52) U.S. Cl.
CPC ............... *A61B 5/24* (2021.01); *A61B 5/259* (2021.01); *A61N 1/0408* (2013.01);
(Continued)

(58) Field of Classification Search
CPC ........... A61B 5/24; A61B 5/259; A61B 5/291; A61B 5/296; A61B 2562/0125;
(Continued)

(56) References Cited

U.S. PATENT DOCUMENTS 4,391,278 A 7/1983 Cahalan
4,409,980 A 10/1983 Yano
(Continued)

FOREIGN PATENT DOCUMENTS

WO WO2009006397 A2 1/2009

OTHER PUBLICATIONS

Kim, Dong-Hwan et al.; Conducting Polymers Grown in Hydrogel Scaffolds Coated on Neutral Prosthetic Devices; published on line on Oct. 27, 2004 in Wiley InterScience (www.interscience.wiley.com).
(Continued)

*Primary Examiner* — Eun Hwa Kim
(74) *Attorney, Agent, or Firm* — Bartony & Associates, LLC

(57) ABSTRACT

An electrode system include a flowable and cohesive surface contact element comprising a hydrophilic polymer swollen with an electrolyte fluid, the contact element having a Q' ratio of at least 5 as defined by the equation $$Q' = \frac{W_W}{W_G}$$

wherein $W_G$ is the dry weight of the hydrophilic polymer and $W_W$ is weight of water in the sample after absorption of the electrolyte fluid comprising water and an electrolyte salt. The surface contact element can consist essentially of the hydrophilic polymer swollen by the electrolyte fluid. Another electrode system includes a contact element including a crosslinked hydrophilic polymer matrix. The contact element has a Q' ratio of at least 5 as defined by the equation
(Continued)

$$Q' = \frac{W_W}{W_G}.$$

The contact elements can also have a Q' ratio of at least 6, at least 7, at least 10 or even at least 11.

17 Claims, 23 Drawing Sheets

Related U.S. Application Data of application No. 12/164,692, filed on Jun. 30, 2008, now Pat. No. 8,706,183.

(60) Provisional application No. 60/937,497, filed on Jun. 28, 2007.

(51) Int. Cl.
*A61B 5/259* (2021.01)
*A61B 5/291* (2021.01)
*A61B 5/296* (2021.01)

(52) U.S. Cl.
CPC .......... *A61N 1/0472* (2013.01); *A61N 1/0496* (2013.01); *A61B 5/291* (2021.01); *A61B 5/296* (2021.01); *A61B 2562/0215* (2017.08); *A61B 2562/0217* (2017.08); *A61B 2562/125* (2013.01); *A61N 1/0484* (2013.01); *A61N 1/0492* (2013.01)

(58) Field of Classification Search
CPC .... A61B 2562/01217; A61B 2562/125; A61N 1/0408; A61N 1/0472; A61N 1/0484; A61N 1/0412; A61N 1/0428; A61N 1/0492
See application file for complete search history.

(56) References Cited

U.S. PATENT DOCUMENTS

| | | | |
|---|---|---|---|
| 4,515,162 A | 5/1985 | Yamamoto | |
| 4,989,607 A | 2/1991 | Keusch | |
| 5,125,405 A | 6/1992 | Schmid | |
| 5,205,297 A | 4/1993 | Montecalvo | |
| 5,223,569 A | 6/1993 | Schmid | |
| 5,405,366 A | 4/1995 | Fox | |
| 5,421,982 A | 6/1995 | Ikeda | |
| 5,582,587 A | 12/1996 | Gyory | |
| 5,622,168 A | 4/1997 | Keusch | |
| 6,673,852 B1 | 1/2004 | Suda | |
| 6,845,272 B1 | 1/2005 | Thomsen | |
| 8,481,059 B2 | 7/2013 | Cleary | |
| 8,706,183 B2 | 4/2014 | Cui | |
| 2005/0197554 A1 | 9/2005 | Polcha | |
| 2006/0015053 A1 | 1/2006 | Crisp | |
| 2006/0165962 A1 | 7/2006 | Borck | |
| 2007/0032719 A1 | 2/2007 | Menon | |
| 2008/0234790 A1 | 9/2008 | Bayer | |
| 2009/0291348 A1 | 11/2009 | Hirashige | |

OTHER PUBLICATIONS

Kanebako, Makoto et al.; Evaluation of Skin Barrier Function Using Direct Current I: Effects of Conductivity, Voltage, Distance Between Electrodes and Electrode Area; Biol. Pharm. Bull; 2002; 25(11); pp. 1456-1460.
Kalia, Yogeshvar N. et al.; Ion Mobility Across Human Stratum Corneum in Vivo; Journal of Pharmaceutical Sciences; Dec. 1998; vol. 87, No. 12, pp. 1508-1511.
Karande, Pankaj et al.; Relationships Between Skin's electrical Impedance and Permeability in the Presence of Chemical Enhancers; Journal of Contolled Release; 2006; 110; pp. 307-313.
Kalia, Yogeshvar N. et al.; Interaction Between Penetration Enhancers and Iontophoresis: Effect on Human Skin Impedance in Vivo; Journal of Controlled Release; 1997; 44; pp. 33-42.
Curdy, Catherine et al.; Non-Invasive Assessment of the Effect of Formulation Excipients on Stratum Corneum Barrier Function in Vivo; International Journal of Pharmaceutics; 2004; 271; pp. 251-256.
Savic, S. et al.; Vehicle-Controlled Effect of Urea on Normal and SLS-Irritated Skin; International Journal of Pharmaceutics; 2004; 271; pp. 269-280.
Landman, Robert J.; Electronics in the Development of Modern Medicine, Aug. 31, 2004; pp. 1-17.
D'Donnell, Matt; Biomedical Instrumentation & Design; BME/EECS 458; Chapter 3; pp. 1-12.
Seitsonen, E. et al.; Are Electrocardiogram Electrodes Acceptable for Electroencephalogram Bispectral Index Monitoring?; Acta Anaesthesiologica Scandinavica; 2000; 44; pp. 1266-1270.
Griss, Patrick et al.; Characterization of Micromachined Spiked Biopotential Electrodes; IEEE Transactions on Biomedical Engineering; Jun. 2002; vol. 49; No. 6; pp. 597-604.
Gondran, C et al.; Non-Polarisable Dry Electrode Based on NASICON Ceramic; Medical & Biological Engineering & Computing; 1995; 33; pp. 452-457.
Griss, Patrick et al.; Micromachined Electrodes for Biopotential Measurements; Journal of Microelectromechanical Systems; Mar. 2001; vol. 10; No. 1; pp. 10-16.
Sohn O, and Kim D; Theoretical and Experimental Investigation of the Swelling Behavior of Sodium Polyacrylate Superabsorbent Particles, Journal of Applied Polymer Science; 2003; vol. 87; pp. 252-257.
McAdams, ET et al.; Factors Affecting Electrode-Gel-Skin Interface Impedance in Electrical Impedance Tomography; Med. & Biol. Eng. & Comput., 1996, 34, pp. 397-408.
Ferree T.C et al.; Scalp Electrode Impedance, Infection Risk, and EEG Data Quality; Clin Neurophys; 2001; 112, pp. 536-544.
Acta Derm Venereol (Stockh) 1992; Suppl. 177, pp. 5, 7, 8, 34-38, 44-46.
Hua F, Mengping Q.; Synthesis of Self-Crosslinking Sodium Polyacrylate Hydrogel and Water-Absorbing Mechanism; Journal of Materials Science; 2001; 36; pp. 731-738.
HUA F.et al.; Preparation of Superabsorbent by Irradiation Polymerization; Journal of East China University of Science and Technology; 1996; vol. 22; No. 3; pp. 362-367.

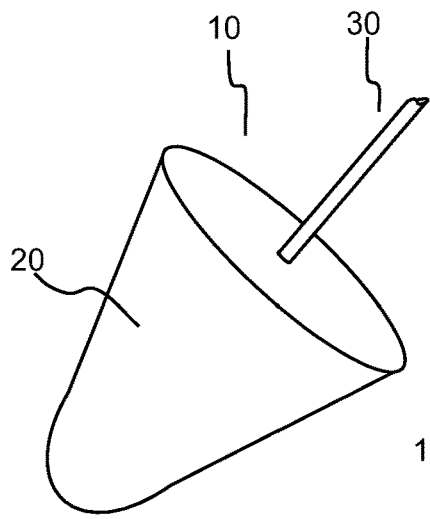
Fig. 1A
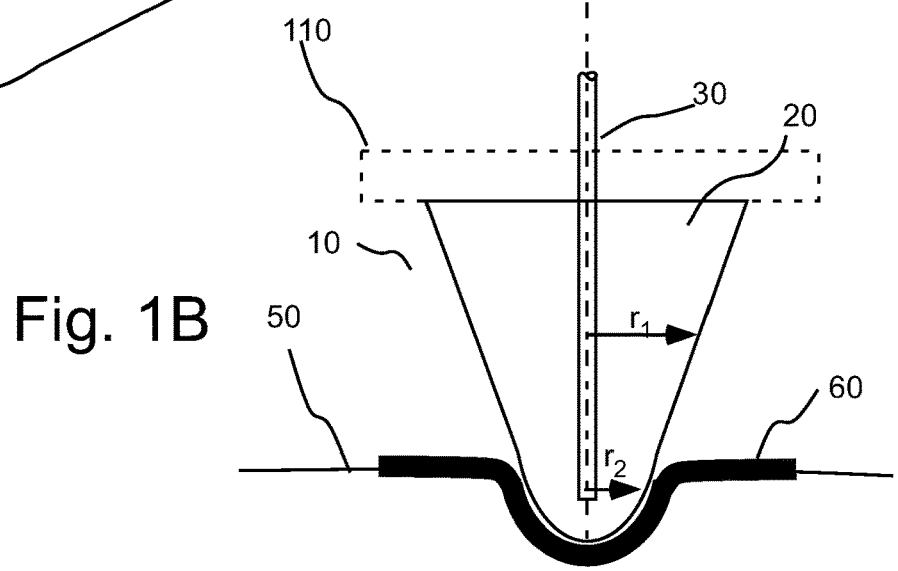
Fig. 1B
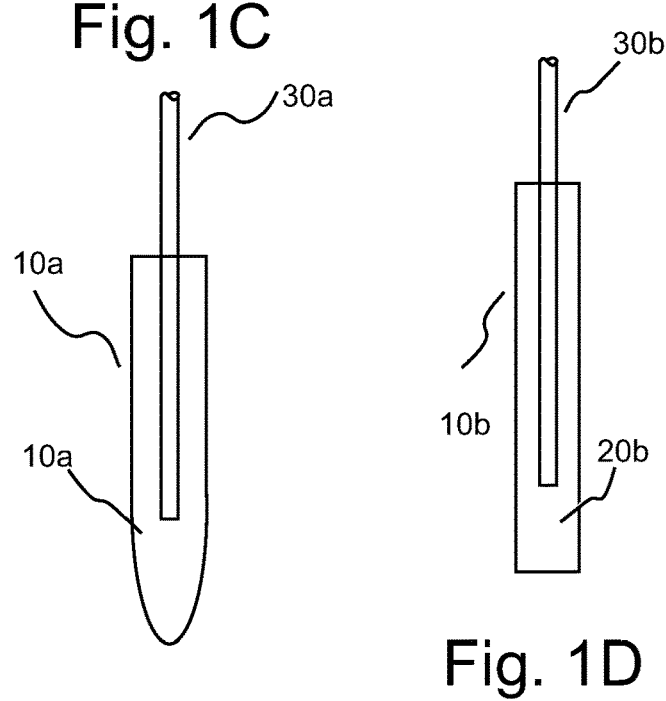
Fig. 1C
Fig. 1D

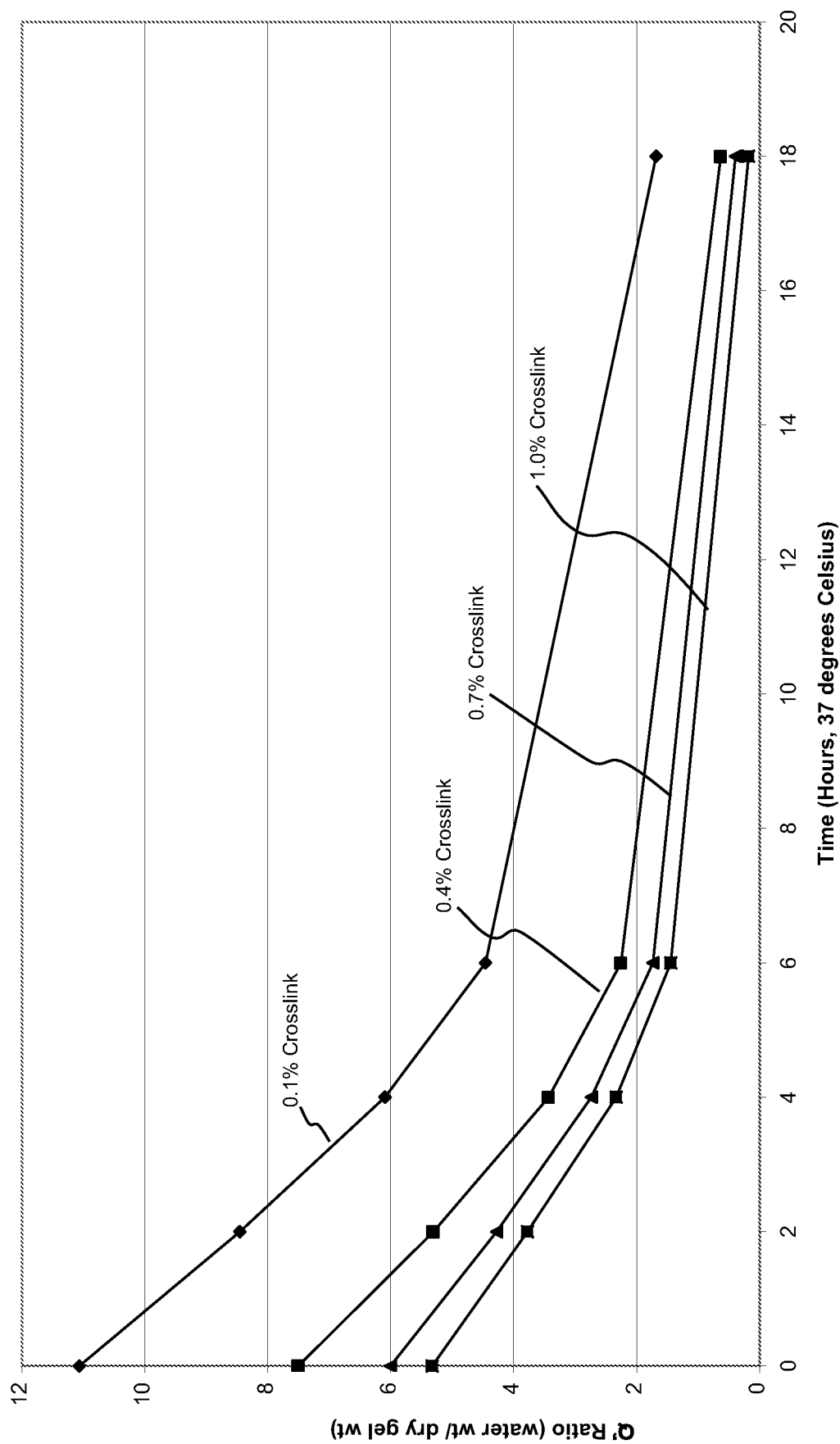

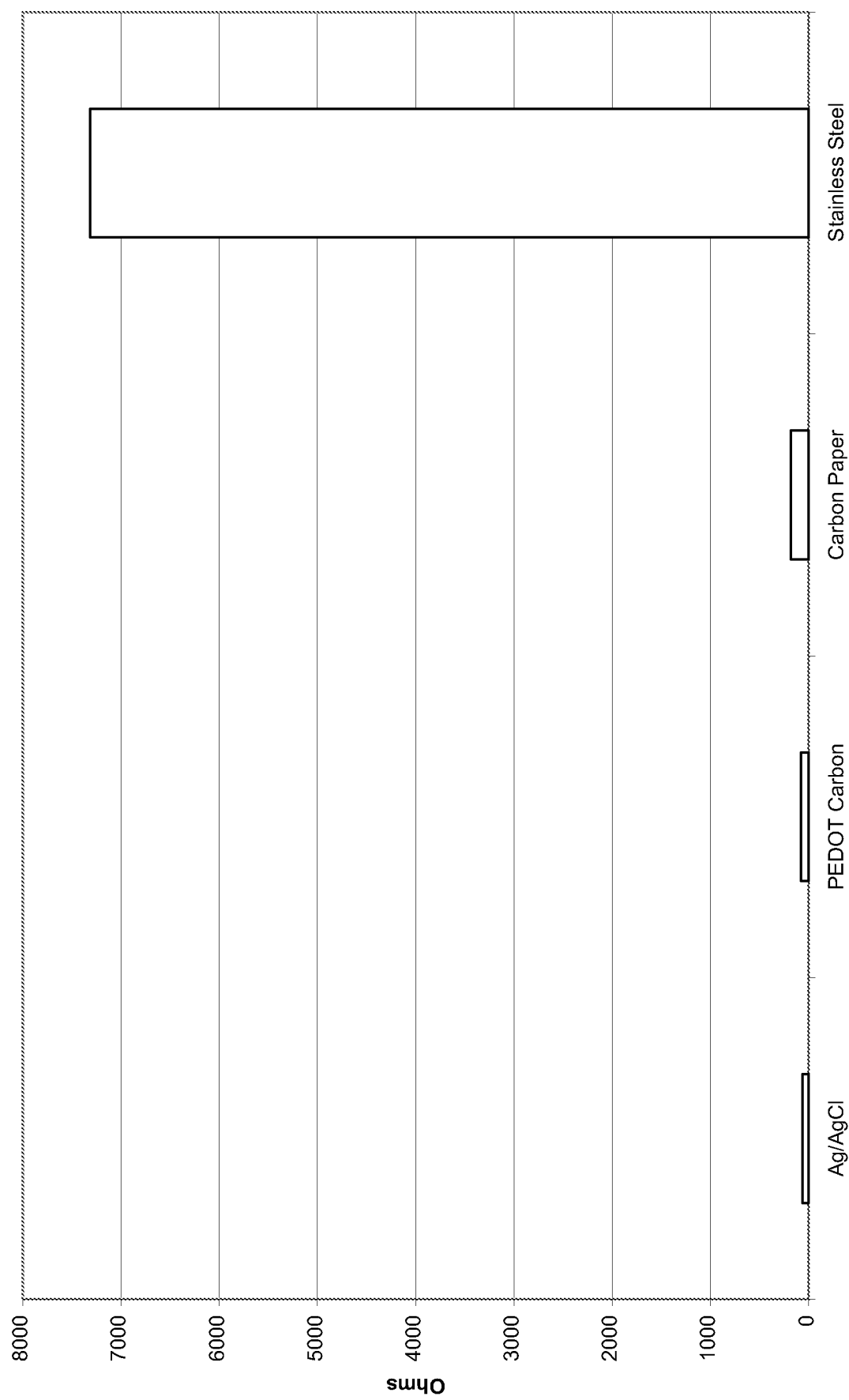

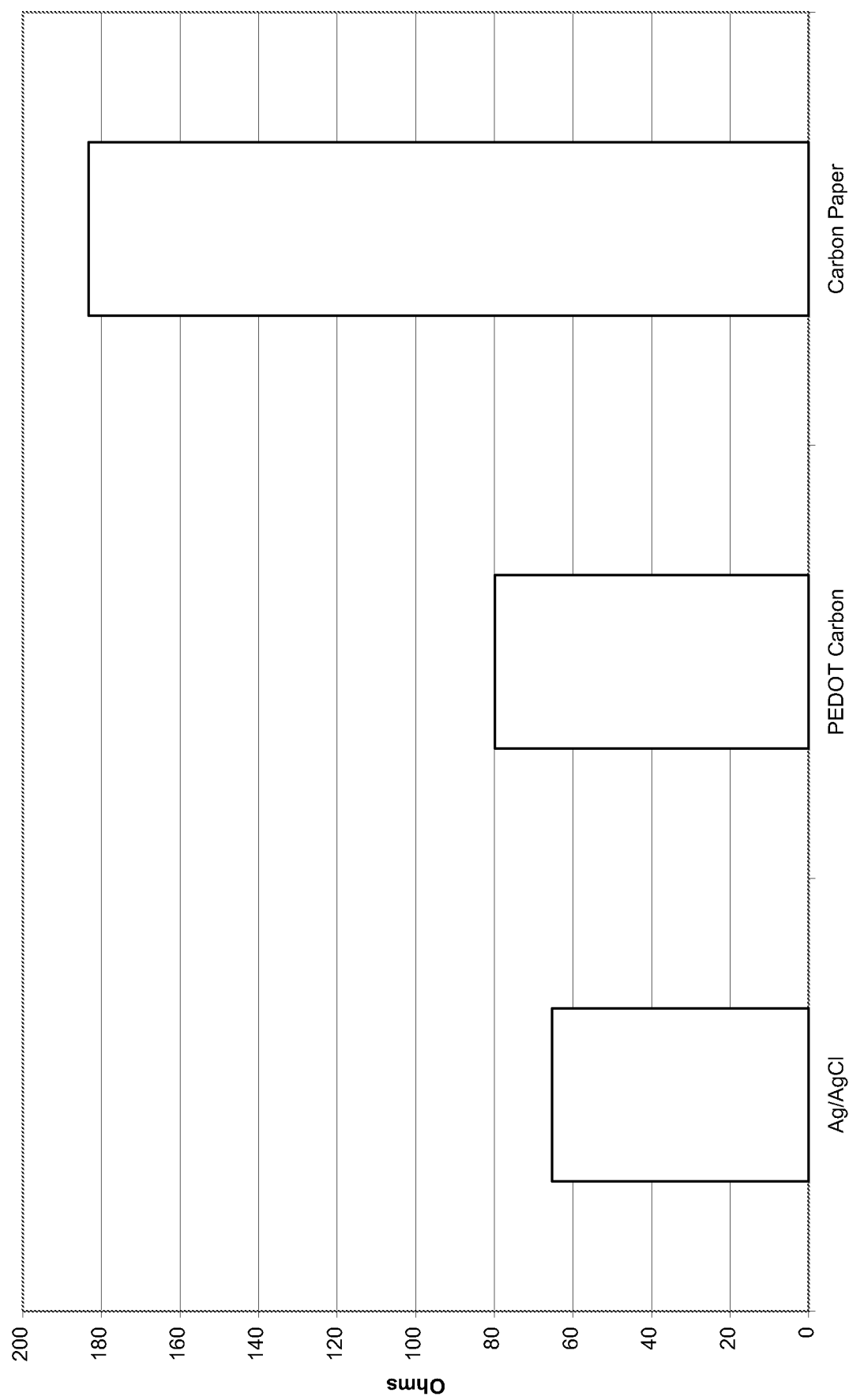

Fig. 21

Table 1

| Time (hours) | Q ratios | | | | % water | | | | |
|---|---|---|---|---|---|---|---|---|---|
| | 0 | 2 | 4 | 6 | 18 | 0 | 2 | 4 | 6 | 18 |
| | 3.536213 | 2.727234 | 1.968234 | 1.429903 | 0.501906 | 77.95518 | 73.17045 | 66.30993 | 58.84609 | 33.41794 |
| | 3.530726 | 2.633434 | 1.820799 | 1.288354 | 0.520413 | 77.92848 | 72.47782 | 64.54906 | 56.30047 | 34.22838 |
| | 3.542297 | 2.744435 | 2.049866 | 1.555209 | 0.590828 | 77.98471 | 73.2937 | 67.21168 | 60.86426 | 37.13966 |
| average | 3.536412 | 2.701701 | 1.9463 | 1.424489 | 0.537716 | 77.95612 | 72.98066 | 66.02356 | 58.67027 | 34.92866 |
| stdev | 0.005788 | 0.059743 | 0.116098 | 0.13351 | 0.046918 | 0.028125 | 0.439806 | 1.354215 | 2.28697 | 1.957192 |
| | 2.988859 | 1.98939 | 1.225995 | 0.821751 | 0.22122 | 74.93018 | 66.54836 | 55.07626 | 45.10775 | 18.11468 |
| | 2.877749 | 2.113555 | 1.450128 | 0.935038 | 0.252174 | 74.21185 | 67.88237 | 59.1858 | 48.32144 | 20.13889 |
| | 3.01536 | 2.224047 | 1.537076 | 1.003708 | 0.29661 | 75.09563 | 68.98308 | 60.58455 | 50.09252 | 22.87582 |
| average | 2.960656 | 2.108997 | 1.4044 | 0.920166 | 0.256668 | 74.74589 | 67.8046 | 58.28221 | 47.84057 | 20.37646 |
| stdev | 0.073012 | 0.117395 | 0.160503 | 0.091886 | 0.037895 | 0.469833 | 1.219222 | 2.863158 | 2.526938 | 2.389441 |
| | 2.683297 | 1.831345 | 1.14154 | 0.733189 | 0.16269 | 72.85041 | 64.6811 | 53.30463 | 42.30288 | 13.99254 |
| | 2.671085 | 1.94109 | 1.210113 | 0.784487 | 0.189494 | 72.7601 | 65.999 | 54.75344 | 43.96149 | 15.93066 |
| | 2.700326 | 1.965255 | 1.319761 | 0.80836 | 0.172096 | 72.97535 | 66.27609 | 56.89211 | 44.70129 | 14.68272 |
| average | 2.684903 | 1.912563 | 1.223805 | 0.775345 | 0.17476 | 72.86195 | 65.65206 | 54.9834 | 43.65522 | 14.86864 |
| stdev | 0.014686 | 0.071367 | 0.089896 | 0.038411 | 0.013599 | 0.108091 | 0.852218 | 1.804761 | 1.228188 | 0.982348 |
| | 2.503801 | 1.716168 | 0.999493 | 0.614293 | 0.040041 | 71.45957 | 63.18343 | 49.98733 | 38.05338 | 3.849903 |
| | 2.515957 | 1.785461 | 1.102246 | 0.705083 | 0.135934 | 71.55825 | 64.0993 | 52.43182 | 41.35182 | 11.9667 |
| | 2.530303 | 1.849046 | 1.201459 | 0.727834 | 0.076319 | 71.67382 | 64.90053 | 54.57558 | 42.12407 | 7.090719 |
| average | 2.516687 | 1.783558 | 1.101066 | 0.682403 | 0.084098 | 71.56388 | 64.06109 | 52.33158 | 40.50975 | 7.635774 |
| stdev | 0.013266 | 0.066459 | 0.100988 | 0.060072 | 0.048418 | 0.107236 | 0.859189 | 2.295769 | 2.162045 | 4.085758 |

ELECTRODE SYSTEMS, DEVICES AND METHODS

CROSS-REFERENCE TO RELATED APPLICATION

This application is a divisional patent application of U.S. patent application Ser. No. 14/196,520, filed Mar. 4, 2014, which is a divisional patent application of U.S. patent application Ser. No. 12/164,692, filed Jun. 30, 2018, now U.S. Pat. No. 8,706,183, issued Apr. 22, 2014, which claims benefit of U.S. Provisional Patent Application Ser. No. 60/937,497, filed Jun. 28, 2007 the disclosures of which are incorporated herein by reference.

BACKGROUND OF THE INVENTION

The present invention relates to electrode systems, devices and methods and, particularly, to electrode systems, devices and methods for use in contact with tissue (for example, skin) for electrophysical measurement.

Skin surface electrodes are important components in many medical diagnostic systems including, for example, electrocardiography (ECG), electromyography (EMG), and electroencephalography (EEG). In these systems, the electrode plays a critical role as a transducer converting physiological variables, such as those of the heart, muscles and brain, respectively, in ECG, EMG and EEG, to electrical potentials (sometime referred to as biopotentials). The measured potentials are then amplified and processed by an instrument, such as an electronic measuring circuit and a computer. The workings of skin surface electrodes are dependant on a multitude of mechanisms, such as electrode material, the electrolyte applied to the electrode, body location, and skin properties. The electrode must convert a physiological ionic current into an electronic current receivable and readable by the associated instrumentation. The electrode commonly used in clinical applications is the silver/silver chloride or Ag/AgCl electrode, which is a non-polarizable electrode that is electrochemically stable and generates relatively little noise. When using standard skin surface electrodes such as the silver/silver chloride electrode, two common preparations are typically required to lower the impedance of the electrode and of the skin contacted by the electrode: 1) an electrolyte gel containing $Cl^-$ ions is applied to maintain good ionic contact with the skin; and 2) the outmost skin layer, stratum corneum, is abraded, because it is the primary barrier to current flow due to its high ionic resistance.

Affixing surface electrodes manually is time-consuming with a high labor cost, thereby increasing medical care expenses. As the number of electrodes increases, which is desirable in, for example, certain EEG data analysis such as Laplacian mapping and source localization, manual placement of individual electrodes can become impractical, regardless of the cost. Automated placement can be desirable in such procedures. There has thus been interest in developing an automated EEG electrode placement system for use in connection with high-resolution EEG applications.

However, EEG electrodes currently used in the clinical setting exhibit a number of problems related to both manual and automatic placement. For example, such EEG electrodes have a flat contact profile with the scalp and must be delivered to the scalp without trapping hairs. In the manual placement case, various ways to handle the hair, such as combing and parting, are performed by hand. In automatic placement, however, such operations are difficult to perform.

Application of electrolyte gel to a large number of electrodes through an automatic system in a reproducible manner is also difficult. In addition, the currently used gel has poor consistency and tends to spread, which could cause interference with neighboring electrodes, especially when high electrode density is required. Further, currently used gels often dry completely in approximately 1 to 2 hours, which presents a problem when long term monitoring (for example, in certain EEG procedures) is desired. Further, the depth of epidermal preparation must be carefully controlled. Otherwise, pain and infection (resulting from over preparation) or high impedance (resulting under preparation) may result. The depth of epidermal preparation is difficult to control automatically. Attempts to reduce or eliminate such problems associated with standard surface electrodes have met with limited success.

It is thus desirable to develop surface electrode systems, devices and methods that reduce or eliminate one or more of the above-identified problems as well as other problems associated with surface electrode systems currently in use.

SUMMARY OF THE INVENTION

In one aspect, the present invention provides an electrode system comprising a flowable and cohesive surface contact element comprising a hydrophilic polymer swollen with an electrolyte fluid, the contact element having a Q' ratio of at least 5 as defined by the equation $$Q' = \frac{W_W}{W_G}$$

wherein $W_G$ is the dry weight of the hydrophilic polymer and $W_W$ is weight of water in the sample after absorption of the electrolyte fluid comprising water and an electrolyte salt. The surface contact element can consist essentially of the hydrophilic polymer swollen by the electrolyte fluid.

The contact element can, for example, include individual particles of crosslinked hydrophilic polymer swollen with electrolyte fluid. The contact element is cohesive in that individual parts tend to cohere or stick together. However, the contact elements are highly hydrated and are not tacky such that they stick or adhere to a surface.

The contact element can have a Q' ratio of at least 6, at least 7, at least 10, or even at least 11. In a number of embodiment, the contact element has a Q' ratio of at least 1.5 even after drying in air at 37° C. for 6 hours. The contact element can a Q' ratio of at least 2.0 after drying in air at 37° C. for 6 hours, or even at least 4.0 after drying in air at 37° C. for 6 hours.

The crosslinked hydrophilic polymer can, for example, include polyacrylate or a derivative of polyacrylate. The polyacrylate can, for example, be sodium polyacrylate, potassium polyacrylate or lithium polyacrylate.

The electrolyte fluid can include a penetration enhancer. The penetration enhancer can, for example, include urea.

The electrode system can further include a conductive electrode element in electrical connection with the contact element. The conductive element can, for example, be nonpolarizable. In several embodiments, the conductive element includes a silver/silver chloride probe. In several other embodiments, the conductive element includes a conductive polymer. The conductive element can, for example, include a conductive substrate coated on at least a portion thereof with a conductive polymer.

The electrode system can further include a holder (for example, a "cup" electrode) formed of a conductive material in which the contact element is at least partially positioned.

In another aspect, the present invention provides a method of applying an electrode system to a surface, including: applying a flowable and cohesive contact element including a hydrophilic polymer swollen with an electrolyte fluid to the surface, the contact element having a Q' ratio of at least 5 as defined by the equation $$Q' = \frac{W_W}{W_G}$$

wherein $W_G$ is the dry weight of the individual particles hydrophilic polymer and $W_W$ is weight of water in the sample after absorption of the electrolyte fluid comprising water and an electrolyte salt. The contact element can consist essentially of a hydrophilic polymer swollen with an electrolyte fluid As described above, the contact element can include individual particles of crosslinked hydrophilic polymer swollen by electrolyte fluid.

The Q' ratio can be least 6, at least 7, at least 10 or even at least 11. In a number of embodiment, the contact element has a Q' ratio of at least 1.5 after drying in air at 37° C. for 6 hours, at least 2.0 after drying in air at 37° C. for 6 hours or even at least 4.0 after drying in air at 37° C. for 6 hours.

As also described above the crosslinked hydrophilic polymer can be or can include polyacrylate or a derivative of polyacrylate. The polyacrylate can, for example, be sodium polyacrylate, potassium polyacrylate or lithium polyacrylate.

The electrolyte fluid can, for example, further include a penetration enhancer. The penetration enhancer can, for example, include urea.

The method can further include placing a conductive electrode element in electrical connection with the contact element. The conductive element can be nonpolarizable. The conductive element can include a silver/silver chloride probe. In several embodiments, the conductive element includes a conductive polymer. The conductive element can, for example, include a conductive substrate coated on at least a portion thereof with a conductive polymer.

The method can, for example, include flowing the contact element into a holder formed of a conductive material so that the contact element is at least partially positioned within the holder.

In another aspect, the present invention provides an electrode system including a contact element including a cross-linked hydrophilic polymer matrix. The contact element has a Q' ratio of at least 5 as defined by the equation $$Q' = \frac{W_W}{W_G}$$

wherein $W_G$ is the dry weight of the crosslinked hydrophilic polymer and $W_W$ is the weight of water in the sample after absorption of an electrolyte fluid comprising water and an electrolyte salt. The contact element can also have a Q' ratio of at least 6, at least 7, at least 10 or even at least 11. In several embodiments, the contact element has a Q' ratio of at least 1.5 after drying in air at 37° C. for 6 hours. The contact element can also have a Q' ratio of at least 2.0, or even at least 4, after drying in air at 37° C. for 6 hours.

In several embodiments, the crosslinked hydrophilic polymer matrix includes (or even consists essentially of) polyacrylate or a derivative of polyacrylate. The polyacrylate can, for example, be sodium polyacrylate, potassium polyacrylate, lithium polyacrylate or combinations thereof.

The electrode system can further include a conductive electrode element in electrical connection with the contact element. The conductive element can be nonpolarizable. The conductive element can, for example, include a silver/silver chloride probe. The conductive element can include a conductive polymer. For example, a conductive probe or substrate can be coated with a conductive polymer. The conductive substrate can, for example, include a metal or conductive carbon.

In several embodiments, the electrolyte solution further includes a penetration enhancer. The penetration enhancer can, for example, include urea.

The contact element can form direct contact (ionic contact) with a surface (for example, a skin surface). Alternatively, the electrode system can further include a flowable and cohesive lower or intermediate contact element (which can also be malleable or formable—that is, capable of being formed into a desire conformation). The intermediate contact element can have a Q' ratio (as defined above) of at least 5. The intermediate contact element can, for example, include individual particles of crosslinked hydrophilic polymer swollen with electrolyte fluid comprising water and an electrolyte salt. The intermediate contact element can have a Q' ratio of at least 6, at least 7, at least 10 or even at least 11. The crosslinked hydrophilic polymer of the particles can include polyacrylate or a derivative of polyacrylate. The polyacrylate can, for example, be sodium polyacrylate, potassium polyacrylate, lithium polyacrylate or combinations thereof. The electrolyte fluid absorbed within the particles can include a penetration enhancer. The penetration enhancer can, for example, include urea.

In another aspect, the present invention provides a method of measuring an electrical signal from living tissue including the act of placing a contact element in ionic contact with the tissue. The contact element has a Q' ratio of at least 5 as defined by the equation $$Q' = \frac{W_W}{W_G}$$

As described above, $W_G$ is the dry weight of the crosslinked hydrophilic polymer, and $W_W$ is the weight of water in the sample after absorption of an electrolyte fluid comprising water and an electrolyte salt. The contact element can have a Q' ratio of at least 6, at least 7, at least 10 or even at least 11. The contact element can have a Q' ratio of at least 1.5 after drying in air at 37° C. for 6 hours. The contact element can also have a Q' ratio of at least 2.0, or even at least 4.0, after drying in air at 37° C. for 6 hours.

The crosslinked hydrophilic polymer matrix can include polyacrylate or a derivative of polyacrylate. The polyacrylate can, for example, be sodium polyacrylate, potassium polyacrylate, lithium polyacrylate or combinations thereof.

The electrode can further include a conductive electrode element in electrical connection with the contact element. The conductive electrode element can be nonpolarizable. The conductive electrode element can, for example, include or be a silver/silver chloride probe. The conductive element can also include a conductive polymer. The conductive polymer can, for example, be coated upon at least a portion of a conductive substrate (for example, a metal or a conductive carbon).

The electrolyte solution can further include a penetration enhancer. The penetration enhancer can include, for example, urea.

In several embodiments, the living tissue is skin and the contact element is placed in connection with the skin without first abrading the skin.

The method can further include placing a lower or intermediate contact element in contact with the tissue between the tissue and the contact element. The intermediate contact element is flowable and cohesive and has a Q' ratio of at least 5. The intermediate contact element can include individual particles of crosslinked hydrophilic polymer swollen with an electrolyte fluid including water and an electrolyte salt. The intermediate contact element can have a Q' ratio of at least 6, of at least 7, of at least 10 or even of at least 11.

The crosslinked hydrophilic polymer of the individual particles can include polyacrylate or a derivative of polyacrylate. The polyacrylate can, for example, be sodium polyacrylate, potassium polyacrylate, lithium polyacrylate or a combination thereof.

The living tissue can, for example, be hair covered skin and the intermediate contact element can be placed in connection with the hair and skin without first abrading the skin and/or without removing the hair.

The electrolyte fluid absorbed within the individual particles can also include a penetration enhancer. The penetration enhancer can, for example, include urea.

In another aspect, the present invention provides an electrode including an electrode element including a conductive polymer. The electrode element can further include a conductive substrate, wherein the conductive polymer is coated on at least a portion of the conductive substrate. The substrate can, for example, include a conductive carbon or a metal. The conductive polymer can, for example, include at least one of polypyrrole, a derivative of polypyrrole, polythiophene, a derivative of polythiopene, polyaniline or a derivative of polyaniline. In several embodiments, the conductive polymer includes poly(3,4-ethylenedioxythiophene) or PEDOT.

Embodiments in which the electrode, including the electrode element, is nonmetallic can, for example, be beneficial in certain uses such as in connection with or in the vicinity of magnetic resonance imaging equipment.

In a further aspect, the present invention provides a method of placing an electrode into ionic contact with tissue including placing a flowable and cohesive contact element including individual particles of crosslinked hydrophilic polymer swollen with electrolyte fluid including water and an electrolyte salt in ionic contact with the skin. As described above, the contact element having a Q' ratio of at least 5 as defined by the equation $$Q' = \frac{W_W}{W_G}$$

$W_G$ is a dry weight of the particles of crosslinked hydrophilic polymer, and $W_W$ is weight of water in the contact element after absorption of an electrolyte fluid comprising water and an electrolyte salt into the particles. The contact element can have a Q' ratio of at least 6, at least 7, at least 10 or even at least 11.

The crosslinked hydrophilic polymer of the individual particles can include polyacrylate or a derivative of polyacrylate. The polyacrylate can, for example, be sodium polyacrylate, potassium polyacrylate, lithium polyacrylate or a combination thereof.

The living tissue can, for example, be hair covered skin and the lower contact element can be placed in connection with the hair and skin without first abrading the skin and/or without removing the hair.

The electrolyte fluid absorbed within the individual particles can include a penetration enhancer. The penetration enhancer can, for example, include urea.

In another aspect, the present invention provides a contact element for use in connection with a surface electrode system comprising a flowable contact element consisting essentially of polyacrylate or a derivative of polyacrylate. The contact element is adapted to absorb an aqueous electrolyte fluid including water and an electrolyte salt so that the contact element has a Q' ratio of at least 5 as defined by the equation $$Q' = \frac{W_W}{W_G}$$

wherein $W_G$ is the dry weight of the crosslinked hydrophilic polymer and $W_W$ is the weight of water in the sample after absorption of the electrolyte fluid.

In another aspect, the present invention provides a surface electrode including an elongated tissue contact member including a crosslinked hydrogel matrix, an electrolyte associated with the hydrogel matrix, and a conductive element in connection with the elongated contact member. The surface electrode can further include at least one conductive polymer incorporated within the hydrogel matrix. The electrolyte can, for example, be an ionic electrolyte comprising an electrolyte salt.

The hydrogel can be synthesized from at least one hydrophilic monomer. The at least one hydrophilic monomer can, for example, be hydroxyethyl methacrylate, acrylic acid acrylamide, N-vinyl-2-pyrrolidone, maleic anhydride, vinyl alcohol or an alkylene oxide. The hydrogel can include at least one of alginate, agar, gelatin and collagen, fibrin, glucosaminaoglycan, chitin or chitosan.

The conductive polymer can, for example, be polymerized within the hydrogel. The conductive polymer can also be polymerized outside the hydrogel and incorporated therein.

The conductive polymer can be polypyrrole, polythiophene, polyaniline or a derivative of such conductive polymers.

The elongated contact member can, for example, have a specific operating impedance on skin of less than 50 $k\Omega*cm^2$, less than k20 $\Omega*cm^2$ or even less than k10 $\Omega*cm^2$.

A radius of the elongated contact member can decrease over at least a portion of the length thereof. The elongated contact member can, for example, have a generally conical or frustoconical shape.

The elongated contact member can include polyacrylate. The elongated contact member can, for example, include poly(hydroxyethyl methacrylate) having polyacrylate incorporated therein.

In a further aspect, the present invention provides a contact element for use in connection with a surface electrode system including a hydrophilic polymer matrix including at least one conductive polymer incorporated within the hydrophilic polymer matrix.

In still a further aspect, the present invention provides a sensor system for measuring electrical activity within at least a portion of a patient's body including at least one electrode or at least one contact element as described above.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 1A illustrates a perspective view of an embodiment of an elongated surface electrode of the present invention having a generally conical shape.

FIG. 1B illustrates a side view of the surface electrode of FIG. 1A in contact with the stratum corneum.

FIG. 1C illustrates a side view of another embodiment of an elongated surface electrode of the present invention having a generally cylindrical shape with a pointed tip.

FIG. 1D illustrates a side view of another embodiment of an elongated surface electrode of the present invention having a generally cylindrical shape.

FIG. 2A illustrates impedance as a function of frequency for a number of electrodes of various compositions both with and without the conducting polymer polypyrrole.

FIG. 11C illustrates the drying studies conducted with a polyacrylate based tissue contact element of the present invention (swelled with an electrolyte solution including 10.7 wt % NaCl) in air at 37° C. wherein the results are set forth as a Q' ratio (water weight/dry gel weight) for several polyacrylates of varying % (w/w) of crosslinker.

FIG. 17A illustrates a comparison of impedance studies for electrodes including an Ag/AgCl electrode element, an electrode element including carbon coated with conducting polymer, a carbon electrode element and a stainless steel electrode element.

FIG. 17B illustrates the data of 16A for electrodes including an Ag/AgCl electrode element, an electrode element including carbon coated with conducting polymer and a carbon electrode element wherein the scale is expanded.

FIG. 21 sets forth Table 1.

DETAILED DESCRIPTION OF THE INVENTION

Figure 2B:
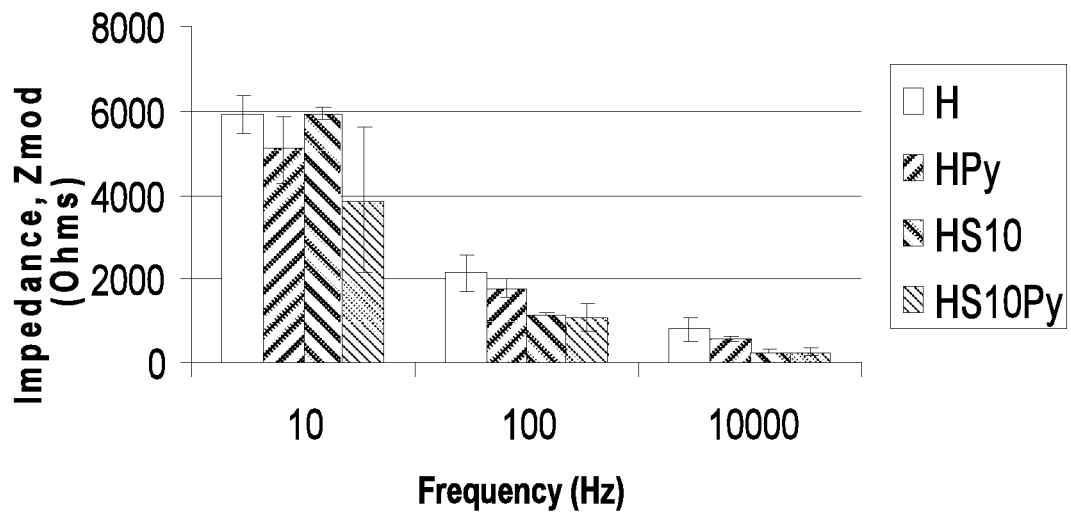
FIG. 2A illustrates impedance as a function of frequency for a number of electrodes of various compositions both with and without the conducting polymer poly(3,4-ethylenedioxythiophene).

The present invention is discussed below in connection with representative examples of surface electrodes for contact with skin/tissue to measure biopotentials or biocurrents. However, one skilled in the art appreciates that the electrodes of the present invention can be used in a variety of manners (particularly were substantial electrode hydration is desirable). Moreover, one skilled in the art appreciates that electrodes of the present invention can also be used to apply a potential or current.

In several embodiments, the present invention provides surface electrodes such as skin surface electrode systems for measuring biopotential such as in EEG, ECG etc. In a number of embodiments, tissue contact portions, sections or elements of electrode systems of the present invention exhibit smaller specific impedance than electrodes currently used in, for example, EEG and ECG. As used herein, the terms "tissue contact element" or "skin contact element" refer to that portion of the surface electrode system in proximity to the tissue/skin that includes an electrolyte to form ionic contact. The tissue contact element can come into direct contact with the tissue/skin or into indirect contact via an intermediate contact element. In several embodiments, tissue contact elements of the present invention exhibit higher aqueous electrolyte content per unit weight and improved moisture retention than electrode contact elements currently in use. Further, the electrode systems of the present invention can require less (or even no) manual skin preparation such as is required with currently available skin surface electrodes. The electrodes of the present invention can replace electrodes currently used to measure biopotentials. Moreover, the electrodes of the present invention can be integrated with automated electrode placing systems (either singularly or in arrays) for use, for example, in multi-channel EEG recording.

In a number of embodiments, the contact elements of the electrodes of the present invention are formed from polymeric materials suitable to form a hydrogel upon contact with an aqueous solution. In general, the hydrogels of the present invention are polymer networks that are water insoluble but highly absorbent of water and aqueous solutions. A function of a conducting hydrogel within a biopotential electrode system of the present invention is to conduct ionic current from underlying tissue to an electrode where signal transduction takes place. The polymer component of a hydrogel serves to hold an aqueous, conductive electrolyte component. The hydrogels of the present invention also serve to effectively increase the contact surface area of the electrode on the tissue by more thoroughly wetting the surface and providing a more intimate contact interface.

To facilitate conduction of ionic current from underlying tissue, the hydrogel preferably exhibits a minimal resistance to ionic current and minimal or no capacitive character. Polarization effects are preferably minimized. Polarization effects can, for example, be reduced by selecting a suitable non-polarizable medium for the inner core electrode or electrode element (at least over the frequency range of interest). In several embodiments the hydrogel is capable of swelling in aqueous electrolyte solution to a significant degree, resists surface drying, and possesses adequate mechanical integrity to compensate for stresses of application and use without damage to the hydrogel.

As described above, the hydrogels of the present invention can be described as a two component system made up of the polymeric matrix component and the contained aqueous electrolyte. The two components are interrelated as aspects of each component can affect properties of the other. For example, the degree of swelling of the polymeric gel is a function of the ionic strength of the electrolyte. Changes in the salt content of the electrolyte can affect gel solution content, dimensions, and mechanical strength.

Many hydrogel-forming polymeric materials can be used in electrodes of the present invention. Such materials can, for example, be safe for skin contact. Such materials also preferably exhibit suitable mechanical and ionic properties. Those skilled in the art can readily determine suitable mechanical and ionic properties for a given use and fabricate electrodes of the present invention to exhibit such properties. Suitable hydrogels can be formed from hydrophilic synthetic polymer networks and/or natural materials. Synthetic polymers suitable to form hydrogels can be made from various monomers including, for example, hydroxyethyl methacrylate, acrylate or acrylic acid, acrylamide, N-vinyl-2-pyrrolidone, maleic anhydride and/or derivatives of such monomers. Poly(vinyl alcohol) and poly(ethylene glycol) can also be used with, for example, an appropriate degree of crosslinking to achieve desired mechanical properties. Materials of natural origin, including, for example, alginate, agar, gelatin and collagen, fibrin, glucosaminaoglycan, chitin and/or chitosan can also be used in forming hydrogels of the present invention. In several studies of the present invention, hydrogels were formed from hydroxyethyl methacrylate or acrylic acid.

A polymeric hydrogel component can, for example, be synthesized from a hydrophilic monomer which is polymerized into a solid mass. As known in the art, the polymerization method can vary with different monomer and initiator systems, as each features a unique degree of efficiency and can require different polymerization environments and time periods to progress to completion. As also known in the art, various concentrations of crosslinking agents can be incorporated as well to increase mechanical integrity and to prevent gel disintegration at large swelling conditions. Typical synthesis methods for poly(hydroxyethyl methacrylate) and polyacrylate used in several studies of the present invention are set forth below.

Poly(hydroxyethyl methacrylate) or pHEMA is a common hydrogel material in use in several important biomedical applications (for example, it is used in soft contact lenses). A polar hydroxyethyl side group moiety contributes to the monomer's hydrophilic character. PHEMA can, for example, be synthesized by diluting HEMA monomer solution in water and then baking the solution in a mold in the presence of an initiator. Many types of initiators suitable for HEMA polymerization exist as know in the art. AIBN (2,2'-azobisisobutyronitrile) is an initiator commonly used in laboratory synthesis and was used in several studies of the present invention.

An example of a protocol for synthesis of pHEMA used in several studies of the present invention follows. HEMA monomer was available in 97% 2-hydroxyethyl methacrylate solution (inhibited with MEHQ). That solution was diluted with deionized laboratory water to some ratio (typically 1:1). This ratio can have an impact on the final morphology of the gel. For example, especially large concentrations of water, such as 85% water to HEMA, can create dramatic changes in structure and appearance. Once the HEMA monomer solution was combined with water an initiator was added, such as 2,2'-azobisisobutyronitrile (AIBN). In the case of AIBN, 1.9 mg of AIBN was added for every 2 mL of 1:1 HEMA/water solution. This mixture was stirred vigorously to ensure that the AIBN solid was completely dissolved into solution.

One or more additives can be introduced to alter the final gel characteristics. Such additives can, for example, include polyacrylate (or other "super absorbent") particles/element to improve swelling, and/or one or more electrically conductive polymers such as PEDOT or polypyrrole to improve impedance characteristics. Once the solution contained the desired composition, it was poured into molds of a desired size and shape (for example, in the shape of the electrodes of FIGS. 1A and 1B), and placed into a laboratory oven to bake at 95° C. for approximately one hour.

A second type of hydrogel used in studies of electrodes of the present invention is polyacrylate. Polyacrylate is a member of a class of materials called "super absorbents" as a result of its polyelectrolyte nature and ability to absorb over 10,000 times its own weight in deionized water. It is commonly found in applications that require fluid holding, such as in diapers and in fire control. As a result of the high moisture content of the material, it typically assumes a mushy paste-like gel morphology when saturated unless chemically crosslinked. Polyacrylate is sensitive to ionic content in solution, and the addition of salts to the gel can reduce the swelled water content. This property can be important in electrode applications as electrolyte solutions are inherently ionic in nature.

Polyacrylate is, for example, synthesized from acrylic acid, a relatively strong simple carboxylic acid. Acrylic acid solutions exhibit a very low pH and were neutralized before being polymerized into a gel. To accomplish this, acrylic acid was first slightly diluted with deionized water with a 4:1 ratio. This solution was then blended with 25.4% (w/w) sodium hydroxide solution until its pH was approximately 5.7. The neutralized solution was then combined with a crosslinking agent and an initiator. In several studies of the present invention, potassium persulfate was used as an initiator at 0.7% (w/w). The concentration of crosslinking agent in the solution directly impacts the final mechanical integrity of the gel; wherein the higher the concentration of crosslinking agent, the greater the modulus of the resulting material. In several studies, N,N'-methylene bisacrylamide (essentially a bifunctional acrylic molecule) was added to the solution at various concentrations ranging from, for example, 0.07% to 1.0% (w/w). This mixture was then poured into the desired mold and baked for 2 hours at 60° C. In several studies, the prepared monomer solution was thoroughly agitated until homogeneous and pipetted in 0.2 mL quantities into 1.5 mL microcentrifuge tubes (Fisher Scientific, Pittsburgh, Pa.), followed by free-radical polymerization at 60° C. for 2 hours.

As discussed above, to improve the electrical characteristics of certain hydrogels, various conducting polymer species can be incorporated into the hydrogel structure using a variety of methods. In several studies of the present invention, the electrically conducting polymers polypyrrole and poly(3,4-ethylenedioxythiophene) or PEDOT were incorporated within the hydrogel matrix. Suitable conducting polymers for use in the present invention include, but are not limited to PEDOT, polypyrrole, polythiophene, polyaniline and/or conductive derivatives of such polymers. The conducting polymer phase may be polymerized directly within the hydrogel itself, or pre-polymerized outside of the gel and incorporated into the gel structure. Each method results in particular final morphology. Such conductive polymers can be incorporated within a pHEMA hydrogel structure with minimal effect on the swelling performance of the hydrogel. A number of studies of the present invention thus involved incorporation of conductive polymer within pHEMA hydrogel. However, conductive polymers can also be successfully incorporated within a polyacrylate and other hydrogel structures.

PEDOT is available commercially in pre-polymerized form suspended in poly(styrene sulfonate) (PSS) solution. The PEDOT/PSS solution can, for example, be added directly to a monomer solution such as a HEMA monomer solution before the HEMA is polymerized into gel. As the HEMA polymerizes, it "locks in" the pre-polymerized PEDOT particles wherever they settled in the solution. This can result in a heterogeneous final structure as the varying densities of the HEMA and PEDOT phases drive them to form layers during the baking process. Such heterogeneous layering may be avoided by polymerizing the PEDOT into fibrous structures and fixing them in the desired locations as the gel polymerizes, resulting in a specific morphology.

Alternatively, a pHEMA or other hydrogel can be swelled in an EDOT, pyrrole or other conducting polymer monomer solution, which is then polymerized in situ. In several studies, 0.01 M EDOT solution was used to swell the gels overnight to maximum capacity, after which the gels were exposed to a saturated FeCl₃ oxidant solution. The treated gels were then baked in a laboratory oven at 30° C. over a period of 30 hours to polymerize the EDOT into PEDOT. In other studies, a 0.1 M pyrrole/0.1 M Cl solution was used to soak the gel, and the polymerization was performed through a dip treatment process, wherein the gel was transferred between various wells of pyrrole, saturated FeCl₃, and deionized water for varying periods of time. Both processes result in a fine dispersion of conductive polymer particles throughout the pHEMA gel, with the highest concentration of particles lying near the surface of the pHEMA. Both conductive polymers provide improvements to the gel electrical performance. However, gels containing PEDOT tended to demonstrate more significant improvement.

In several studies of the present invention, a number of different electrode compositions were fabricated to study the effect of introduction of conducting polymer and/or highly absorbent polyacrylate into a polyHEMA matrix. In the studies of FIGS. 2 though 8 described below, the following compositions were investigated: polyHEMA (H), polyHEMA+sodium polyacrylate (HSxx, wherein xx refers to the quantity, in milligrams, of polyacrylate used in the batch preparation), polyHEMA+polypyrrole (HPy), polyHEMA+polypyrrole+polyacrylate/(HSxxPy), polyHEMA+PEDOT (HPe), and polyHEMA+PEDOT+polyacrylate (HSxxPe). Tissue contact elements 20 (formed from a hydrogel matrix as described above) of electrodes 10 were formed around a conducting connecting wire, connector or probe 30 in a generally conical mold as illustrated in FIGS. 1A and 1B.

Impedance can be described as the complex resistance encountered by a signal flowing from the patient through the electrode to a monitor. Typically, lower impedances will result in a better signal trace. The concept of electrical impedance generalizes Ohm's law to AC circuit analysis. Electrochemical Impedance Spectroscopy (EIS) was used to investigate the impedance characteristics of various hydrogel-based electrodes of the present invention. In several studies, impedance measurements were made (1) in phosphate buffered saline (PBS) solution (pH 7.2) and (2) on the surface of a skin sample harvested from a large adult pig. The skin harvesting was approved by the University of Pittsburgh Institutional Animal Care and Use Committee (IACUC).

In several studies of the present invention, a two-electrode setup was used with an Ag/AgCl electrode (normally used for ECG) as the reference/counter electrode, and the tapered or pointed ($r_1 > r_2$) electrodes 10 (FIGS. 1A and 1B) as the working electrode, on surgically removed pig skin. The region of pig skin to which the Ag/AgCl reference electrode was applied was thoroughly cleansed with alcohol pads and abraded until the outermost stratum corneal layer was removed. The working electrodes were applied on both prepared and unprepared skin regions as described below. The elongated, pointed and/or tapered shape of electrodes 10 did well in penetrating the fine hairs of the pig skin studied, saving the step of hair parting in the skin preparation as required with conventional EEG electrodes. Other elongated electrodes such as electrodes 10a and 10b illustrated in FIGS. 1C and 1D, respectively, can be used to penetrate hairs. In FIGS. 1C and 1D, like components are numbered similarly to corresponding components in FIGS. 1A and 1B with the addition of the designation "a" and the designation "b", respectively.

Figure 2A:
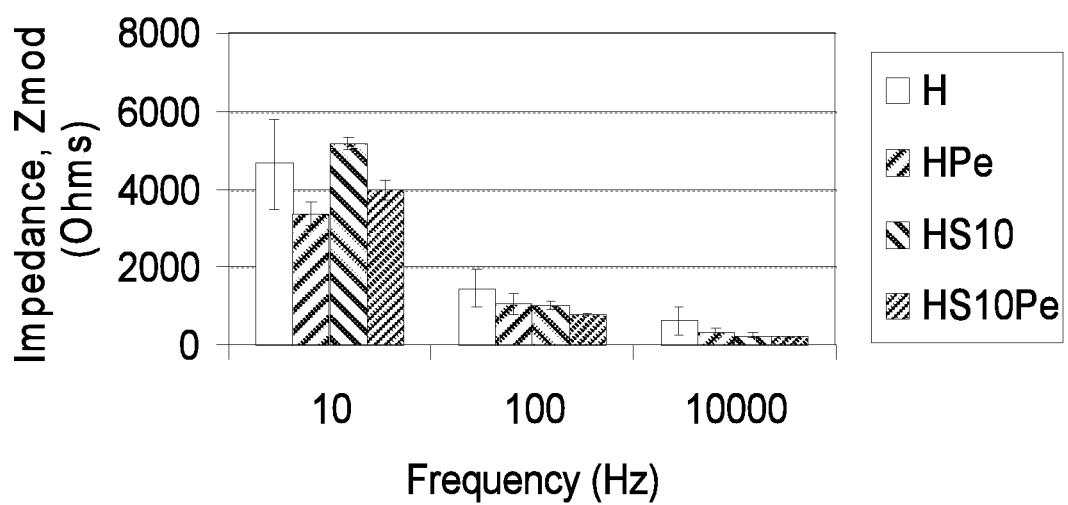
Figure 3:
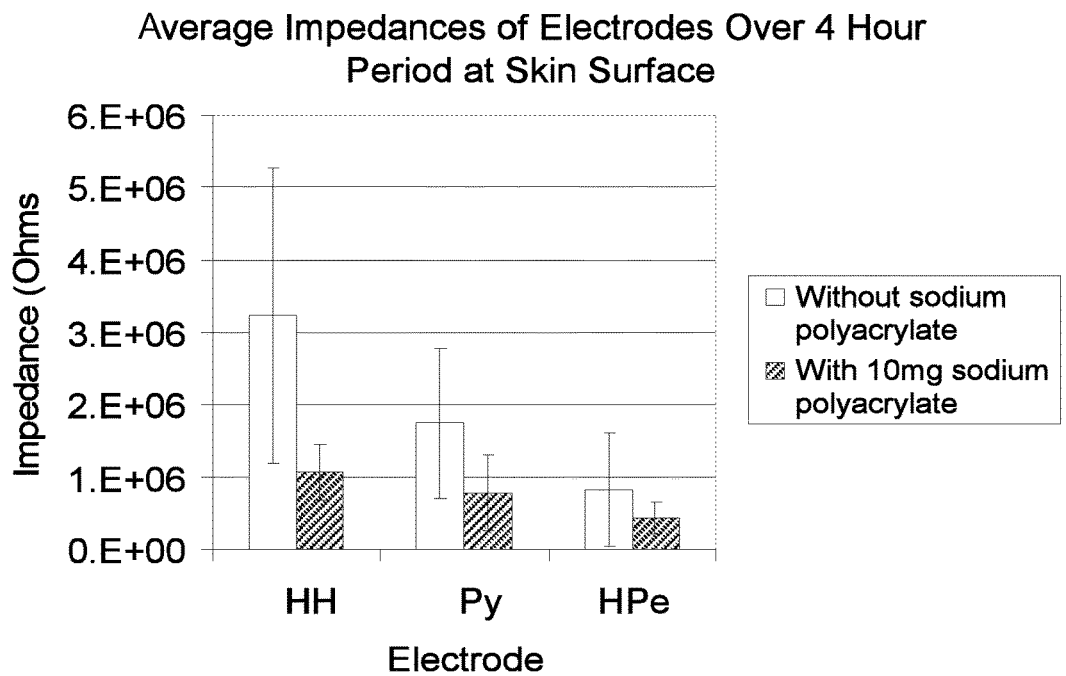
FIG. 3 illustrates average impedance for electrodes including poly(hydroxyethyl methacrylate) with and without the conducting polymers poly(3,4-ethylenedioxythiophene) and polypyrrole.

In several studies, impedance measurements were made between the two electrodes (working and counter) for the frequency range or 1 Hz to 100 kHz. Impedance decreases with increasing frequency. As illustrated in FIGS. 2A and 2B, respectively, conductive polymers PEDOT and polypyrrole effectively decrease the impedance as measured in PBS at each frequency tested. As illustrated, for example, in FIG. 3, incorporation of conductive polymers and polyacrylate into the hydrogel effectively decreases impedance at the skin-electrode interface. Impedance values set forth in FIG. 3 were determined at a frequency of 14.63 Hz.

Figure 4:
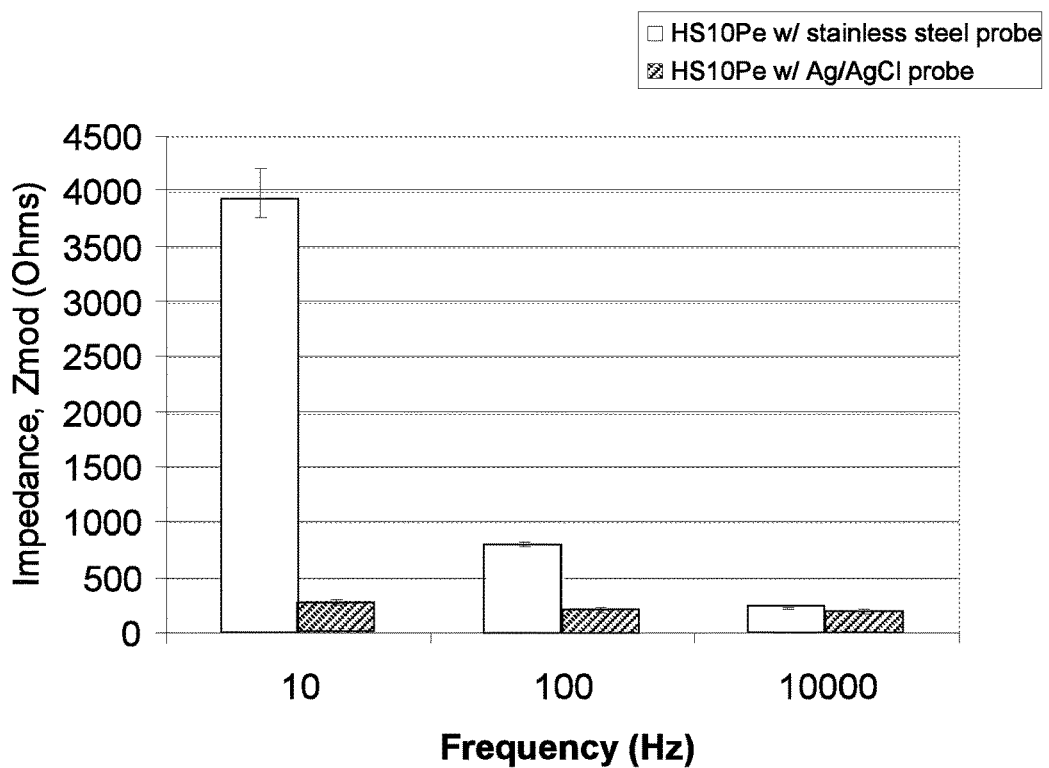
FIG. 4 illustrates electrochemical impedance spectroscopy studies of electrodes of the present invention with stainless steel and silver/silver chloride electrical connectors or probes.
Figure 5:
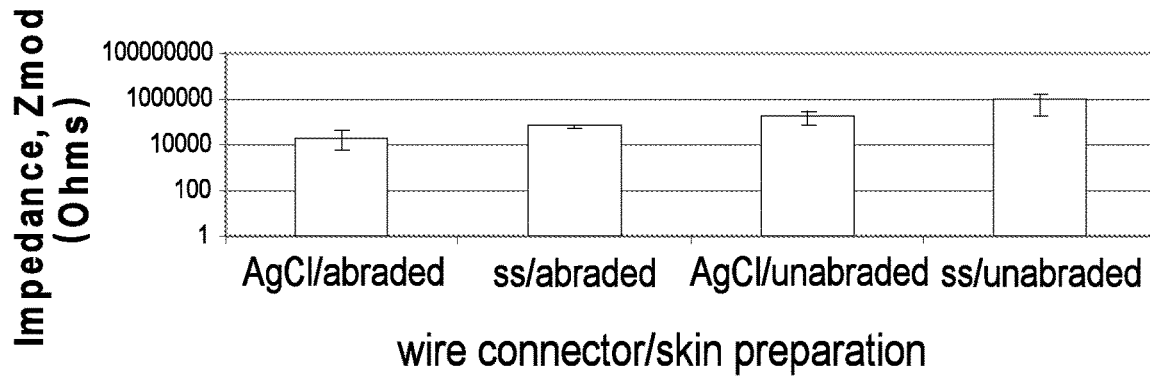
FIG. 5 illustrates electrochemical impedance spectroscopy studies of electrodes of the present invention with stainless steel and silver/silver chloride electrical connectors in connection with unabraded and abraded skin.

As illustrated in FIG. 4, use of a Ag/AgCl probe in place of a stainless steel wire as connecting wire 30 (see FIGS. 1A and 1B) significantly reduced the impedance associated with the electrode for EIS measurements in PBS. As illustrated in FIG. 5, lower impedances for abraded skin indicates significant contribution of stratum corneum layer 50 of the skin to the overall impedances. FIG. 5 also once again illustrates that for EIS measurements at the skin surface, hydrogel electrodes 10 with inserted Ag/AgCl probes as connecting wire 30 demonstrated lower impedances than electrodes including connecting wires 30 of stainless steel wires.

One or more reagents 60 can be used in connection with electrodes of the present invention to make the skin more permeable to ions. Such reagents 60, sometimes referred to as "penetration enhancers" are, for example, described in McAdams, Medical & Biological Engineering & Computing (1996), the disclosure of which is incorporated herein by reference. That paper provides a number of penetration enhancer mechanisms, though most of those mechanisms are not well understood. Typically, less aggressive penetration enhancers act by altering the hydration of the stratum corneum or altering the packing structure of ordered lipids or intercellular channels. More aggressive penetration enhancers physically destroy or dissolve lipids directly. The safest penetration enhancer is water. In that regard, hydration causes cells to swell, and the normally tight packing of cells is loosened, rendering skin more permeable. Contrary to results set forth in the present studies, however, it is indicated that hydration typically has little influence on capacitive properties.

Many penetration enhancers used in electrolytic gels are surfactants, which are absorbed at water/oil interfaces via orientation of the surfactant groups. Surfactants facilitate transition between polar and non-polar phases.

A widely used penetration enhancer in drug delivery is the dipolar aprotic solvent dimethylsulphoxide (DMSO). Other sulphoxides are also used (for example, decyl MSO, as well as amides such as dimethylamide (DMA), dimethylacetamide (DMAC), and dimethylformamide (DMF)). Cyclic amides have also been used as penetration enhancers (for example, 2-NMP, 2-P, and Azone). Although applications of concentrated DMSO have been found to reduce barrier properties of skin by up to 95%, the treatment is very aggressive and has irreversible effects.

Esters of saturated or unsaturated fatty acids (for example, oleic acid, myristic acid, and capric acid) have been indicated to be useful as penetration enhancers. Other, relatively mild penetration enhancers include propylene glycol, ethanol, urea, and sodium lauryl sulphate, as well as various natural oils including eucalyptus, chinopodium, carvone, and 1,8-cineole. Sodium lauryl sulphate, for example, has been shown effective at reducing parallel resistance (up to 95% for a 0.2% solution). Any of the penetration enhancers described above as well as other penetration enhancers can be used in connection with the electrode systems of the present invention.

Figure 6:
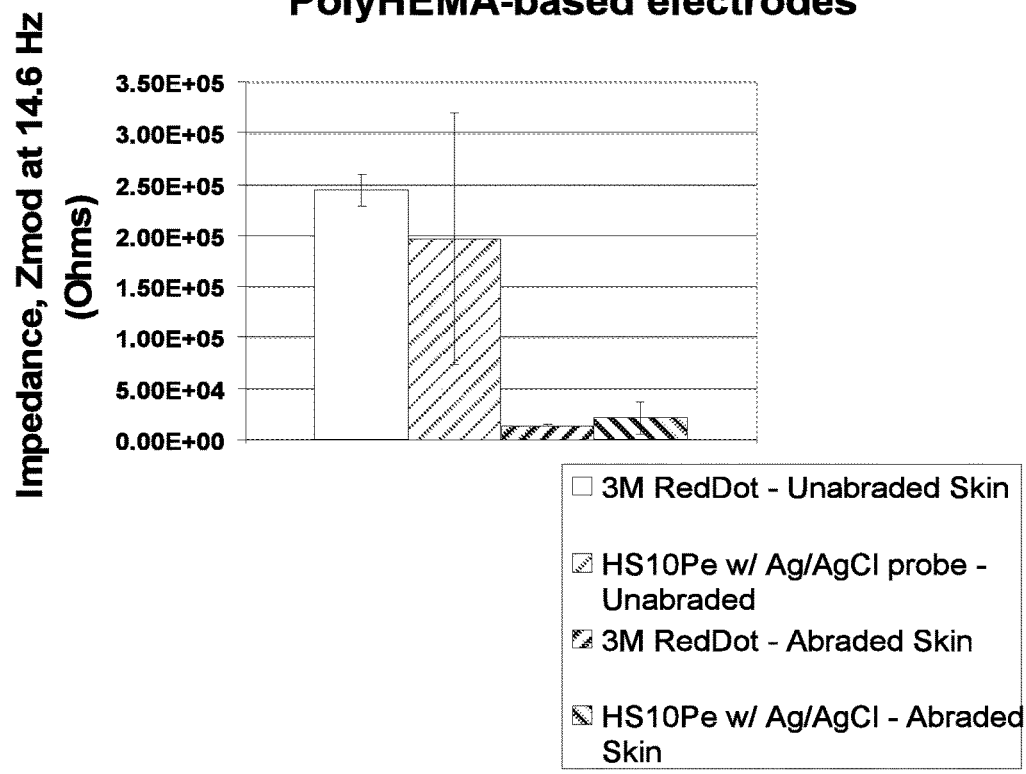
FIG. 6 illustrates a comparison of impedance of a commercially available skin surface electrode and electrodes of the present invention at a frequency of 14.6 Hz.

In a number of studies, impedance of several electrodes of the present invention were compared to 3M™ RED DOT™ electrodes available from 3M of Saint Paul, Minn. As illustrated in FIG. 6, HS10Pe electrodes with Ag/AgCl connecting wires performed just as well as conventional Ag/AgCl 3M RED DOT electrodes at the skin surface. Thus, EIS studies at the skin surface indicate that although the electrodes of the present invention have a significantly smaller skin contact area (less than one-tenth) compared to the RED DOT conventional Ag/AgCl biopotential electrodes, the impedances are similar within the 1 to 100 Hz frequency range (FIG. 6). The specific impedances ($\Omega*cm^2$) of the electrodes of the present invention are, therefore, approximately an order of magnitude smaller than the commercially available biopotential 3M RED DOT electrode.

Figure 7:
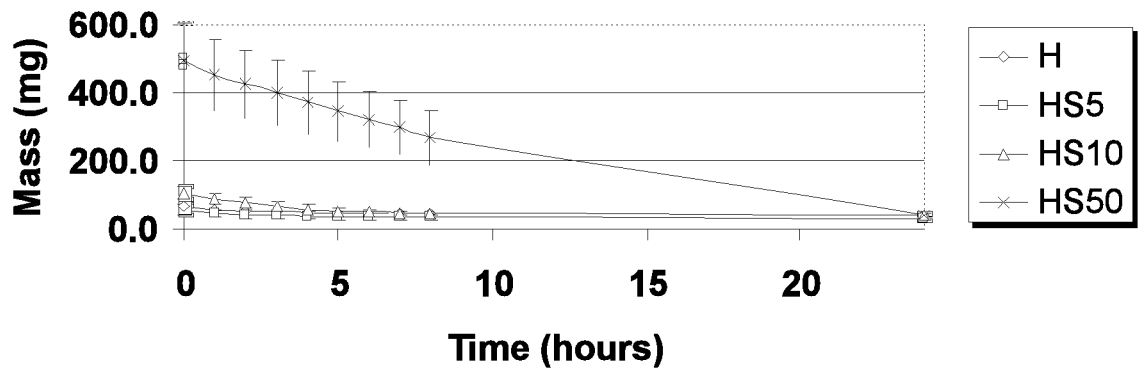
FIG. 7 illustrates dehydration studies of several electrodes of the present invention.

The present studies have also shown that maintenance of hydration is important to facilitate good ionic mobility, as well as to achieve and/or to maintain low impedance. Different hydrogel compositions as described above were studied to determine dehydration properties. As also described above, polyacrylate is highly absorbent of water and was incorporated into the hydrogel of the electrodes of the present invention to facilitate greater water retention, thus promoting enhanced ion mobility and reduced impedances. As illustrated in FIG. 7, increasing the concentration of polyacrylate in the polyHEMA electrode preparation improves the water retention characteristic of the electrode. Once again, the numbers 5, 10 and 50 as set forth in FIG. 7 represent the quantity (in milligrams) of polyacrylate used in the batch preparation.

Figure 8:
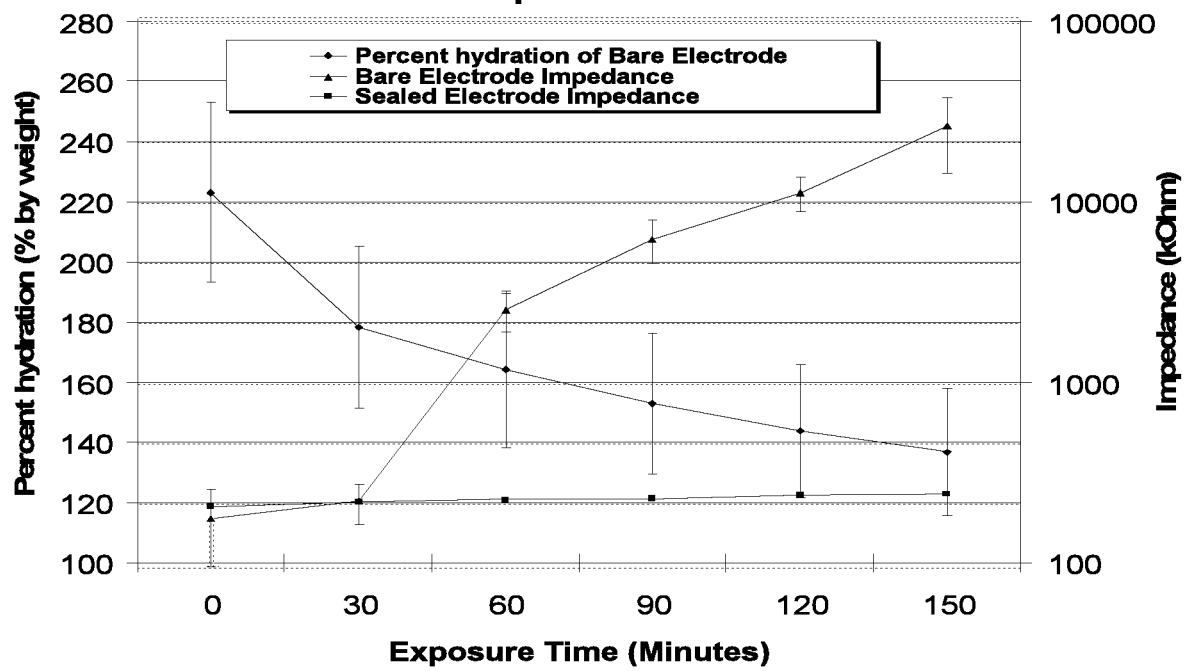
FIG. 8 illustrates the relationship between dehydration characteristics of electrodes of the present invention and impedance thereof.

As illustrated in FIG. 8, increasing impedance over time is associated with drying of exposed hydrogel electrodes, resulting in reduced ionic mobility. By reducing the exposure of the electrodes to air, the rate of drying can be effectively decreased.

Figure 9A:
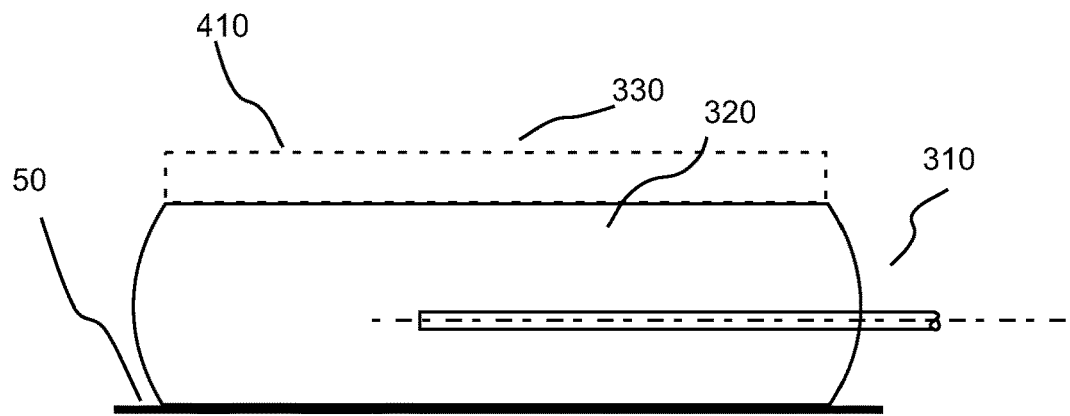
FIG. 9A illustrates an embodiment of surface electrode of the present invention wherein the tissue contact element of the surface electrode is formed from a highly absorbent hydrophilic polymer matrix.

To further study the effects of improved hydration on electrode performance, electrodes in which the polymer matrix of the skin contact element included 100% polyacrylate were fabricated and tested. An embodiment of such an electrode 310 is illustrated in FIG. 9A. The tissue contact element 320 of electrode 310 was formed from crosslinked polyacrylate which was swelled in an appropriate electrolytic solution (for example, a solution with the ionic strength of 10× phosphate-buffered saline). In several studies of electrodes of the present invention, a silver/silver chloride (Ag/AgCl) connecting electrode element 330 was used.

In forming the electrodes, crosslinked sodium polyacrylate gel was synthesized using a method based on a protocol set forth in Sohn O, and Kim D; Theoretical and Experimental Investigation of the Swelling Behavior of Sodium Polyacrylate Superabsorbent Particles, Journal of Applied Polymer Science vol 87, 252-257 (2003), the disclosure of which is incorporated herein by reference. Sohn describes the mechanical and swelling behavior of sodium polyacrylate particles polymerized through an inverse suspension technique. In the present studies; tissue/skin contact element 320 were formed as hydrogel pads by polymerization of a sodium polyacrylate composition within shaped molds, rather than through suspension as disclosed in Sohn supra.

In one such example, acrylic acid (20.8 g) was first diluted with deionized laboratory water (5.2 g). The diluted acrylic acid solution was then neutralized with a prepared 25.4% (w/w) sodium hydroxide aqueous solution (35 g) to a pH of 5.7. A crosslinking agent, N,N'-methylene bisacrylamide, was added to the solution to 0.1% (w/w) concentration. In several embodiments, crosslinking agents suitable for use in the present invention include a compound or compounds including at least two unsaturated groups suitable to undergo a free radical polymerization with the hydrogel monomer or monomers. A 0.1% (w/w) concentration of crosslinking agent resulted in a gel that was cohesive and pliable yet maintained excellent swelling characteristics. As clear to one skilled in the art, various alternative concentrations can be employed with varying effects on mechanical behavior. See, for example, Sohn supra. In several embodiments of the present invention, crosslinker concentration can vary, for example, between approximately 0.05% (w/w) and 1.0% (w/w) (based on the total volume of the precursor solution—that is, total weight of acrylic acid, water, sodium hydroxide solution, etc.). Finally, potassium persulfate was added to the monomer solution (to achieve a 0.8% (w/w) concentration) as an initiator. All reagents were provided by Sigma-Aldrich, Milwaukee, Wis. The prepared monomer solution was thoroughly agitated until homogeneous and pipetted in 0.2 mL quantities into 1.5 mL microcentrifuge tubes (available from Fisher Scientific, Pittsburgh, Pa.). Free-radical polymerization was then carried out at 60° C. for 2 hours. After 2 hours, the resulting crosslinked gels were allowed to cool and were removed from the microcentrifuge tubes with a metal tool.

In general, the polyacrylate tissue contact elements of the present invention exhibited a Young's modulus or modulus of elasticity in the range of approximately 1-10 kPa when a 0.1% crosslinker concentration was used in synthesis (as measured by atomic force microscopy (AFM) microindentation as known in the art). Desirable mechanical properties (modulus and elongation to failure) for such tissue contact element can, for example, correspond generally to those of wet disposable contact lenses.

Mechanical properties such as modulus of elasticity, elongation to failure, tear resistance and fracture toughness can be adjusted/increased by changing/increasing crosslinker concentration. In general, crosslinker concentration in the range of approximate 0.1 to 0.4 wt % provided acceptable results. However, increasing crosslinker concentration can also reduce the amount of electrolyte fluid absorbed by the resultant polymer matrix. Several polyacrylate tissue contact elements of the present invention were synthesized using crosslinker concentration of 0.1%, 0.4%, 0.7%, and 1% and subsequently swelled in, for example, 10.7% NaCl solution.

As described above, to gain an appreciable conductive character, polyacrylate contact elements 320 were swelled in an appropriate aqueous electrolytic solution. As clear to one skilled in the art, the nature of the ionic solution can effect the final characteristics of the hydrogel. Polyacrylates and other hydrogels typically swell to a greater degree in deionized water as compared the degree of swelling in certain ionic solutions, as a result of changes in osmotic pressure. Initial studies were performed to determine the utility of various solutions. Although many different electrolyte solutions can be used, it was found that a good balance of electrical, mechanical, and fluid-holding performance was achieved using, for example, a solution with the ionic strength of 10× phosphate-buffered saline. In general, many electrolyte salts can be used in the electrodes of the present invention. Examples include, but are not limited to, sodium chloride, potassium chloride, magnesium chloride etc. The weight percent of the electrolyte salt in the electrolyte solution can, for example, vary between approximately 0.5 wt % or 1.0 wt % up to the solubility limit of the electrolyte salt. In several studies, to minimize possible ionic interactions, solutions with composition using only pure aqueous sodium chloride at concentration of 10.7% (w/w) was used. A 10.7% NaCl solution has an ionic strength approximately equivalent to that of 10×PBS, without the large variety of ion species present in 10×PBS. While a concentrations of 10.7% is significantly higher than normal physiological sodium chloride concentration, repeated experiments revealed no resulting skin irritation and consistent results over time.

To evaluate the efficacy of a urea additive (penetration enhancer) on electrolyte performance, a solution was prepared by combining a volume of the 9.1% (w/w) sodium chloride solution with 15% (w/w) pure dry urea powder (available from EMD Chemicals Inc, Gibbstown, N.J.), which was stirred until completely dissolved. The weight percents provided are based upon the total weight of the solution. While this concentration of urea is greater than that found in most consumer cosmetic products, it is well within a range considered safe for topical use. During the course of the studies of the present invention, no adverse skin reaction or irritation was observed at any point in time on any subject wherein urea was used, even after many hours of exposure.

To evaluate the capacity for swelling or water/electrolyte fluid retention of the prepared polyacrylate gel contact elements 320, their behavior in was first studied for contact elements swelled with deionized laboratory water. Five unswelled polyacrylate samples were immersed in deionized water and allowed to take in water until swelled to maximum capacity over the course of 24 hours. The swelled polyacrylate samples were then removed from the water bath and weighed using a Fisher Accu-224 analytical balance at time zero and again after various time intervals while being exposed to room temperature air (23° C.). A final measurement was taken after 142 hours of air exposure. The measurement at 142 hours of air exposure was assumed to represent the weight of a completely dehydrated sample. Water content within the hydrogels at each time point (t) can, for example, be represented by a water content ratio $Q_t$, defined as the weight of absorbed water divided by the dehydrated sample weight, as shown in eq. (1) below:

$$Q_t = \frac{W_t - W_0}{W_0} \quad (1)$$

In equation (1), $W_0$ is the dehydrated sample weight and $W_t$ is the total weight of the sample at time t. $Q_t$ is analogous to the water uptake ratio described by Sohn, supra.

Similarly, water or electrolyte fluid (EF) content can be defined in terms of weight percent as set forth in equation (2) below:

$$Wt\ \%_t = 100 * \left(\frac{W_t - W_0}{W_t}\right) \quad (2)$$

Figure 10A:
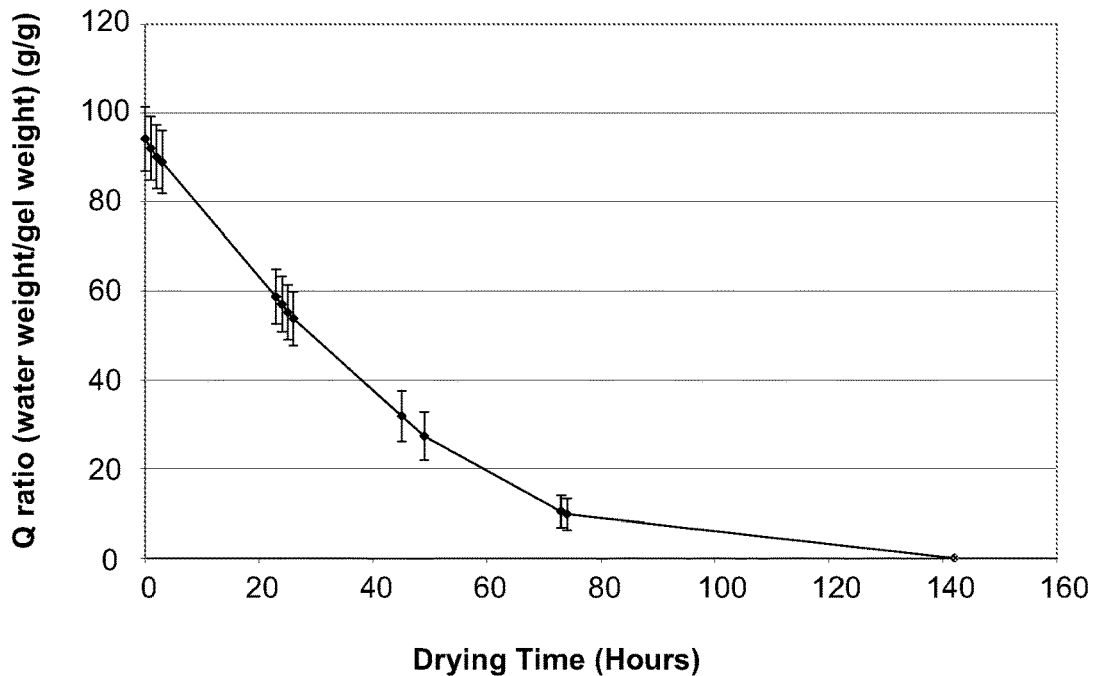
FIG. 10A illustrates a drying study conducted with a polyacrylate based tissue contact element of the present invention (swelled with deionized water) in air at room temperature wherein the results are set forth as a Q ratio (water weight/gel weight).
Figure 10B:
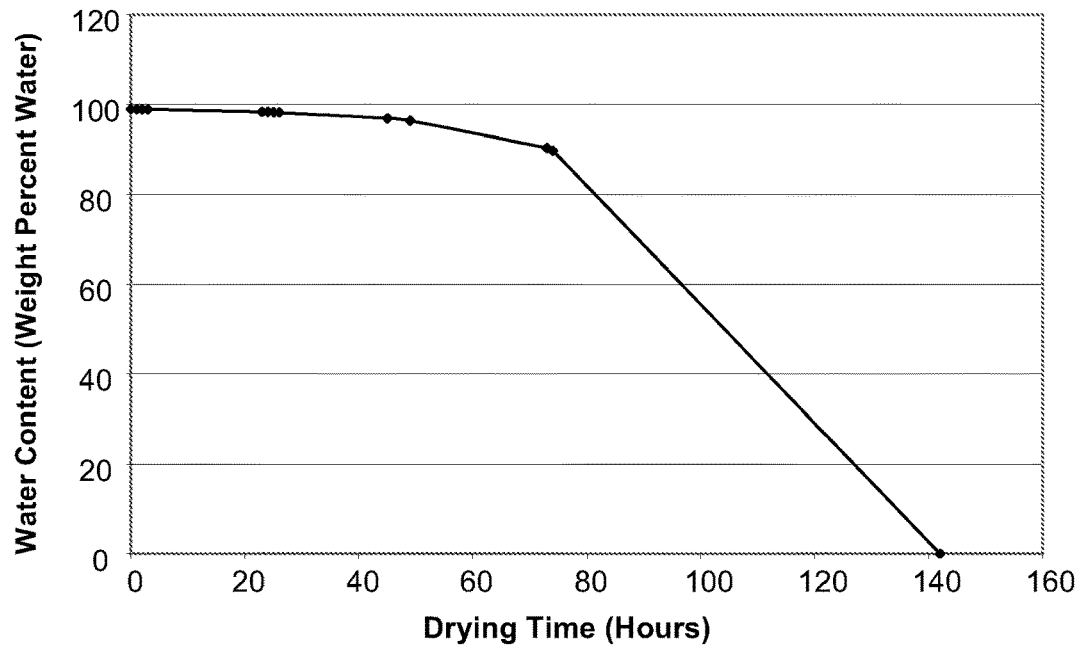
FIG. 10B illustrates a drying study conducted with a polyacrylate-based tissue contact element of the present invention (swelled with deionized water) in air at room temperature wherein the results are set forth as a weight percent water.

Using the above equations, straightforward visualization can be produced illustrating both maximum fluid content of the hydrogel contact elements as well as fluid loss over time as the gels are exposed to air. As illustrated in FIG. 10A, initial $Q_t$ values for experiments with deionized water were above 90 and remained above 20 until approximately 60 hours of drying in open air at approximately 22° C. (room temperature). The samples were dried in open air within a plastic weighing boat. As illustrated in FIG. 10B, initial Wt $\%_t$ values were above 99% and remained above 95% after 40 hours of drying. Water content did not drop below 80% until after 70 hours of drying. Impedance was found to remain relatively constant over a wide range of Wt % water content in several studies.

Figure 10C:
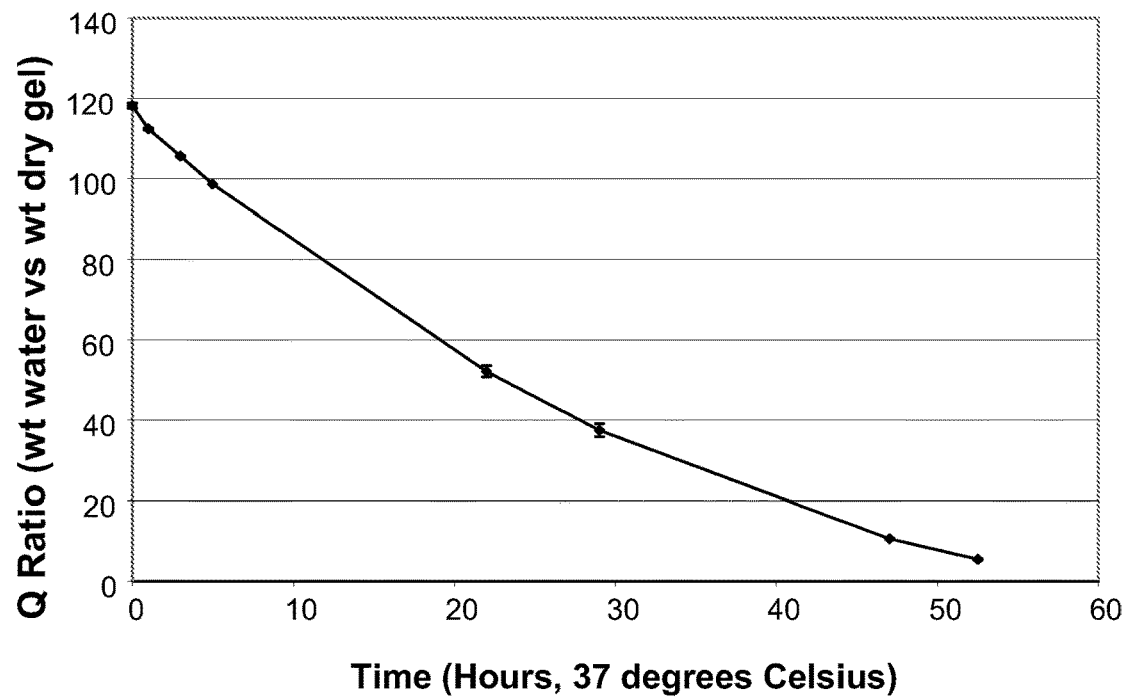
FIG. 10C illustrates a drying study conducted with a polyacrylate based tissue contact element of the present invention (swelled with deionized water) in air at 37° C. wherein the results are set forth as a Q ratio.
Figure 10D:
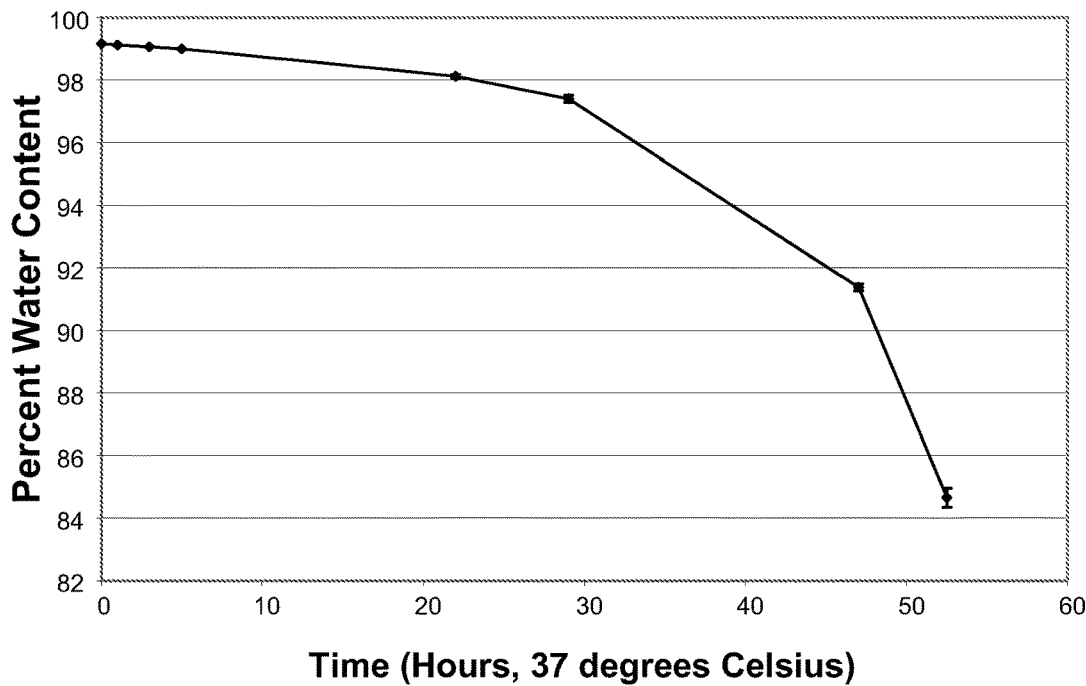
FIG. 10D illustrates a drying study conducted with a polyacrylate-based tissue contact element of the present invention (swelled with deionized water) in air at 37° C. wherein the results are set forth as weight percent water.

To model drying of the tissue contact elements of the present invention when used in connection with tissue, drying experiments were conducted in air in an oven at 37° C. (98.6° F.) and approximately 40% humidity. Such drying conditions are actually substantially more severe than the drying conditions experienced in common use of the electrodes of the present invention when used as skin surface electrodes. FIGS. 10C and 10D set forth drying studies of polyacrylate-based tissue contact elements (0.1% cross-linker concentration) swelled with deionized water wherein the results are set forth as Q values (water weight/gel weight) and percent water, respectively. The increased drying temperature changed the shape of the drying curve. In general, the percent water content curve illustrated in FIG. 10D has the same shape as that of FIG. 10B, but the timescale of drying is shifted.

Figure 11A:
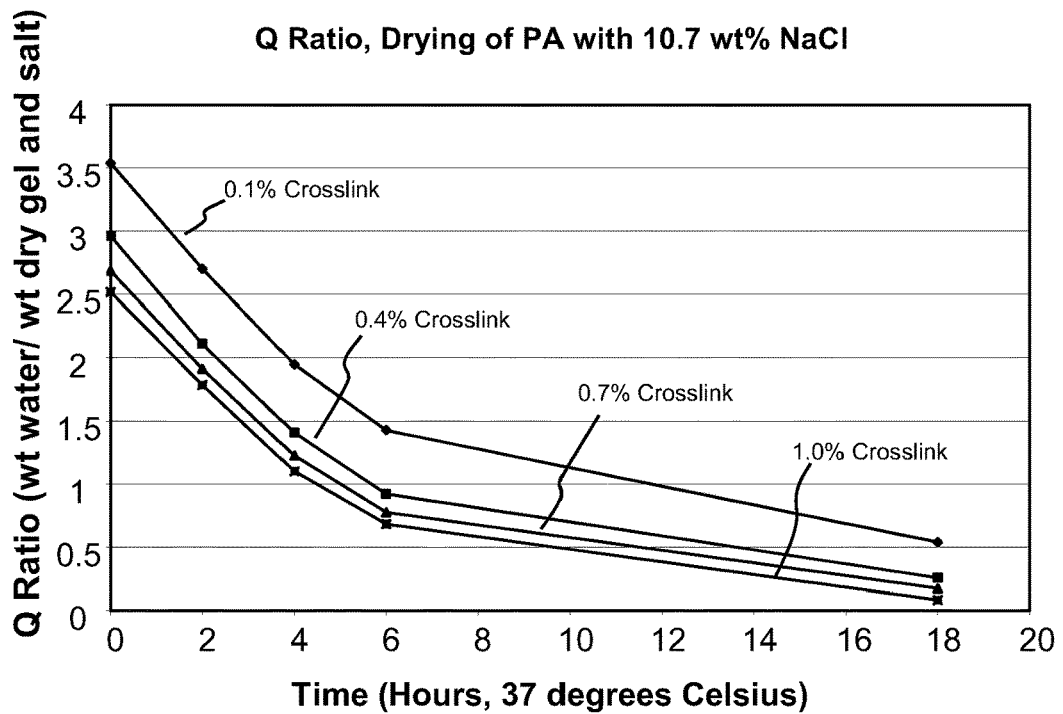
FIG. 11A illustrates a drying study conducted with a polyacrylate based tissue contact element of the present invention (swelled with an electrolyte solution including 10.7% (weight/weight or w/w) NaCl) in air at 37° C. wherein the results are set forth as a Q ratio (water weight/(dry gel weight plus weight of salt)) for several polyacrylates of varying % (w/w) of crosslinker.
Figure 11B:
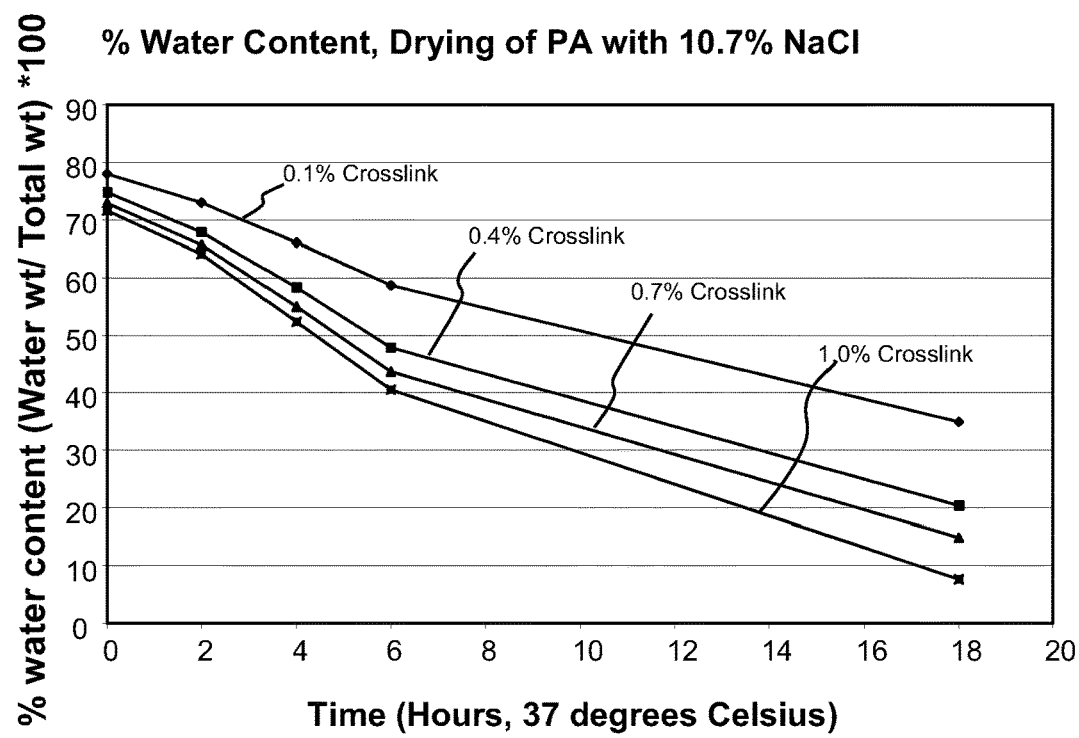
FIG. 11B illustrates a drying study conducted with a polyacrylate based tissue contact element of the present invention (swelled with an electrolyte solution including 10.7 wt % NaCl) in air at 37° C. wherein the results are set forth as weight percent water for several polyacrylates of varying % (w/w) of crosslinker.

FIG. 11A through 11C illustrate drying studies conducted with a polyacrylate-based tissue contact element of the present invention swelled with an electrolyte solution (10.7 wt % NaCl) in air at 37° C. (at approximately 40% humidity) as described above in connection with FIGS. 10D and 10E. Each of FIGS. 11A and 11B set forth results for polyacrylate-based tissue contact elements of varying wt % of crosslinker. The data for the studies of FIGS. 11A through 11C is set forth in Table 1 of FIG. 21. In FIG. 11A, the results are set forth as a Q ratio (water weight/(dry gel weight plus electrolyte salt weight)). In FIG. 11B, the results are set forth as a weight percent water (based upon total weight–water, electrolyte salt and dry gel). In FIG. 11C the data are set forth as a modified Q ratio or Q' ratio wherein Q' is defines as:

$$Q'_t = \frac{W_W}{W_G} \quad (2)$$

In equation (2), $W_W$ is the sample water weight at time t and $W_G$ is the weight of the dry gel. The weight of the salt is excluded in this equation. $Q'_t$ thus provides a good measure of the hydration of the sample at a given time.

As described above, the degree of swelling in ionic solutions can be less than in deionized water. The initial swelled weight percents of water for polyacrylate tissue contact elements synthesized with 1.0%, 0.7%, 0.4% and 0.1% crosslinker were approximately 72%, 73%, 75%, and 78% respectively. Ignoring the weight of the electrolyte salt, initial swelled weight percents of water for polyacrylate tissue contact elements synthesized with 1.0%, 0.7%, 0.4% and 0.1% crosslinker were approximately 83%, 85%, 87%, and 91% respectively. The initial Q' ratios for polyacrylate tissue contact elements synthesized with 1.0%, 0.7%, 0.4% and 0.1% crosslinker were approximately 5.3, 6.0, 7.5 and 11.1 respectively.

Performing drying studies with gels swelled with electrolyte solution can be difficult. In that regard, as water evaporates from the gel, salts are left behind and the salt concentration within the gel becomes effectively saturated, resulting in an osmotic pressure within the gel as the gel shrinks (as a result of high salt concentration). After the solution saturates, salt begins precipitating as solid crystals along the outer surface of the gel, effectively forming a shell which can block further evaporation. In FIGS. 11A through 11C, a deviation in the drying curve occurs after approximately 6 hours, which can be a result of precipitation of salt on the surface of the tissue contact elements. In that regard, salt precipitation was observable after approximately 10 hours of drying. However, the drying curves over at least the first six to eight hours of drying provide a valid study. In the studied of FIGS. 11A and 11B, three individual gels of each crosslink density as determined by crosslinker concentration (0.1%, 0.4%, 0.7%, and 1% crosslinker concentration) were placed into an oven at 37° C. An average value at each time for each crosslinker concentration is plotted in FIGS. 11A through 11C.

In several other studies, functional electrode samples were prepared by immersing unswelled polyacrylate in either a sodium chloride electrolyte bath or a sodium chloride plus urea electrolyte bath. The polyacrylate was allowed to swell completely over a course of, for example, 12 hours. The electrolyte bath was prepared to contain a composition of either 10.7% (w/w) sodium chloride or 9.1% (w/w) sodium chloride and 15% (w/w) urea, as described above. Once the polyacrylate was completely swelled, it was sectioned using a razor blade into small disks or contact elements 320, each approximately 3 mm thick and 10 mm in diameter. Contact elements 320 were then perforated along the long axis thereof with a sharp metal point which was then removed, creating a channel across the diameter of contact elements 320 through which a 0.8 mm thick silver/silver chloride electrode element 330 was inserted (available from World Precision Instruments Inc., Sarasota, Fla.). Resultant hydrogel electrode disks 310 could, for example, be applied flat against a skin surface and secured in place with an adhesive bandage or surgical tape (represented, for example, as biasing element 410 in FIG. 9A), leaving silver/silver chloride electrode element 330 lead wire exposed for recording. An image of an electrode 310 alongside a currently available EEG electrode is set forth in FIG. 11C.

As described above, there are various techniques to reduce stratum corneum impedance. These methods include, for example, skin hydration, electroporation, chemical treatment, physical abrasion and combinations thereof. In several embodiments of the present invention, skin hydration (via the use of tissue contact elements having a high electrolyte fluid content) was selected, to provide a simple and practical method to reduce impedance. To assess the electrical performance of electrodes 310 on human skin, the inner forearm surface was selected for an initial model. The inner forearm has been used in a number of previous studies for investigations on skin barrier properties, and has been found to be a convenient and consistent representation of skin performance. There is, however, variability in skin barrier performance with changing skin thickness, body location, moisture content, hair density or pore density. Thus, the quantitative results of any such test can only be considered a base estimate of actual performance during, for example, EEG recording. Studies of the present invention include data collected from several individual subjects and forearm locations. Comparison testing performed using equipment and subjects employed in the studies of the present invention revealed that average non-abraded forehead skin impedance was roughly two orders of magnitude lower than inner forearm non-abraded impedance, measured using commercially available EEG electrodes and the electrodes of the present invention.

Figure 12:
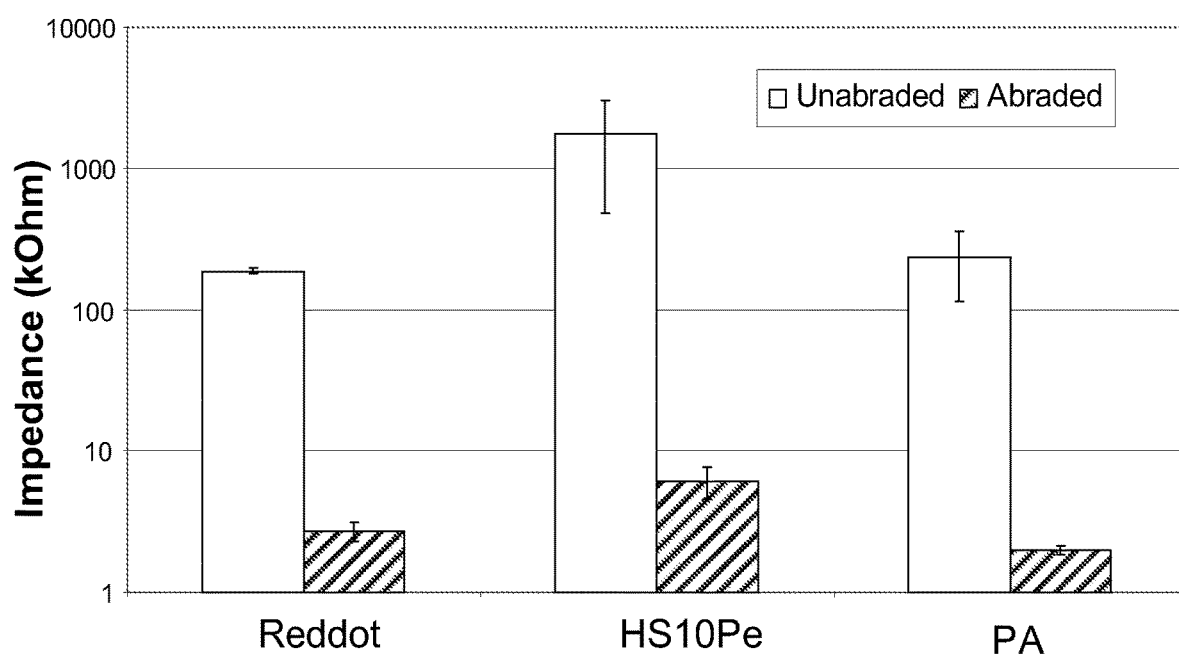
FIG. 12 illustrates an impedance study on both unabraded and abraded human forearm skin comparing impedance of a 3M™ RED DOT™ electrode available from 3M of Saint Paul, Minn., an electrode of the present invention wherein the tissue contact element is formed from poly(hydroxyethyl methacrylate) with the conductive polymer PEDOT and polyacrylate therein, and an electrode of the present invention wherein the tissue contact element is formed from polyacrylate.

FIG. 12 illustrates a comparison of impedances of a 3M RED DOT, a HS10Pe electrode of the present invention as described above and a polyacrylate (PA) electrode of the present invention for both unabraded and abraded skin. As illustrated, the electrodes of the present invention compare favorably with the currently available electrode. The highly hydrated polyacrylate electrodes of the present invention perform particularly well in comparison with currently available surface electrodes.

Figure 13A:
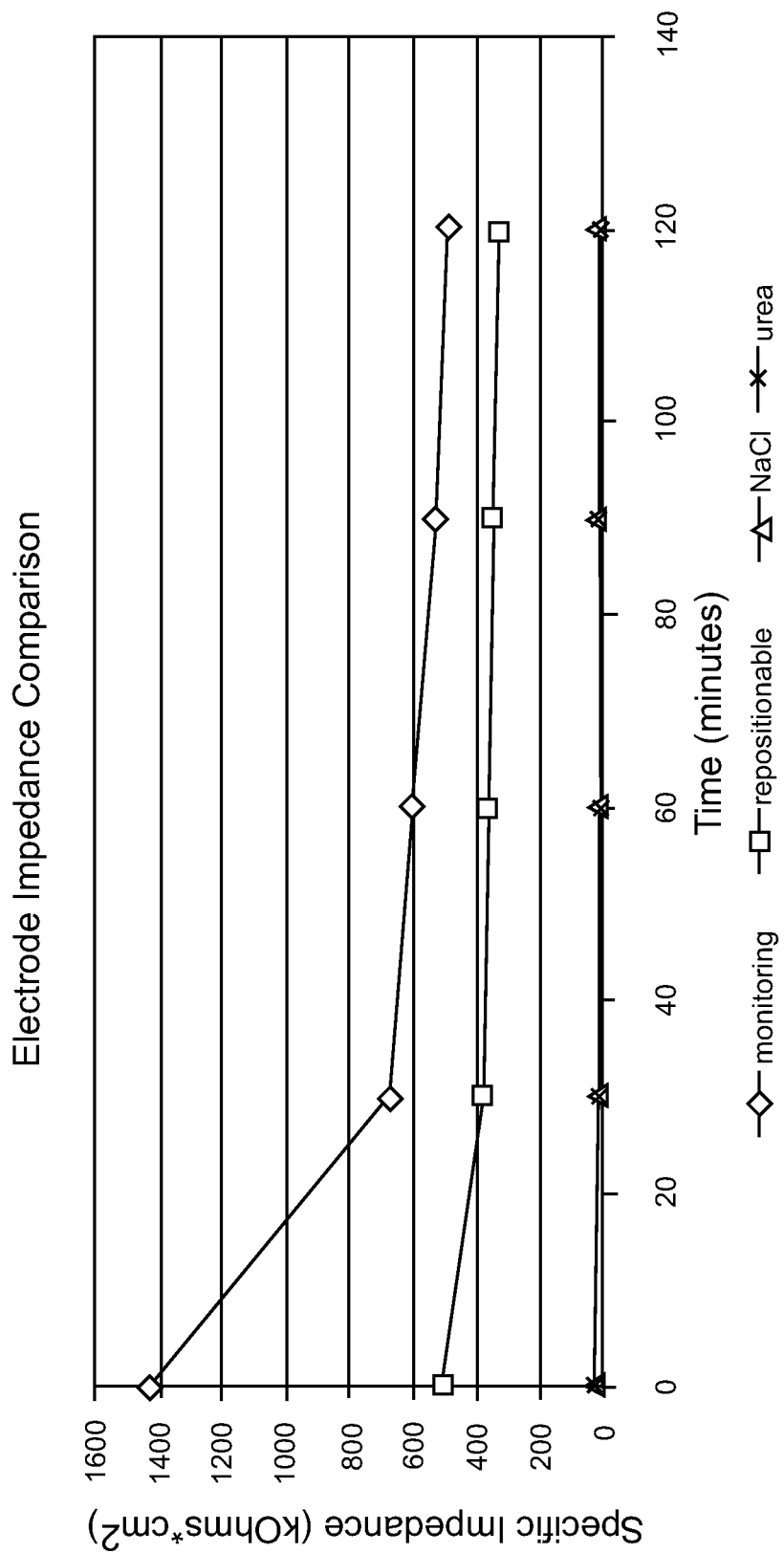
FIG. 13A illustrates a study of specific impedance as a function of time for a commercially available 3M Red Dot 2760 Repositionable Monitoring Electrode, a commercially available 3M Red Dot 2570 Radiolucent Monitoring Electrode, a polyacrylate electrode of the present invention without urea in the absorbed electrolyte fluid and a polyacrylate electrode of the present invention with urea in the absorbed electrolyte fluid, on human forearm without skin preparation, using two-point impedance spectroscopy.
Figure 13B:
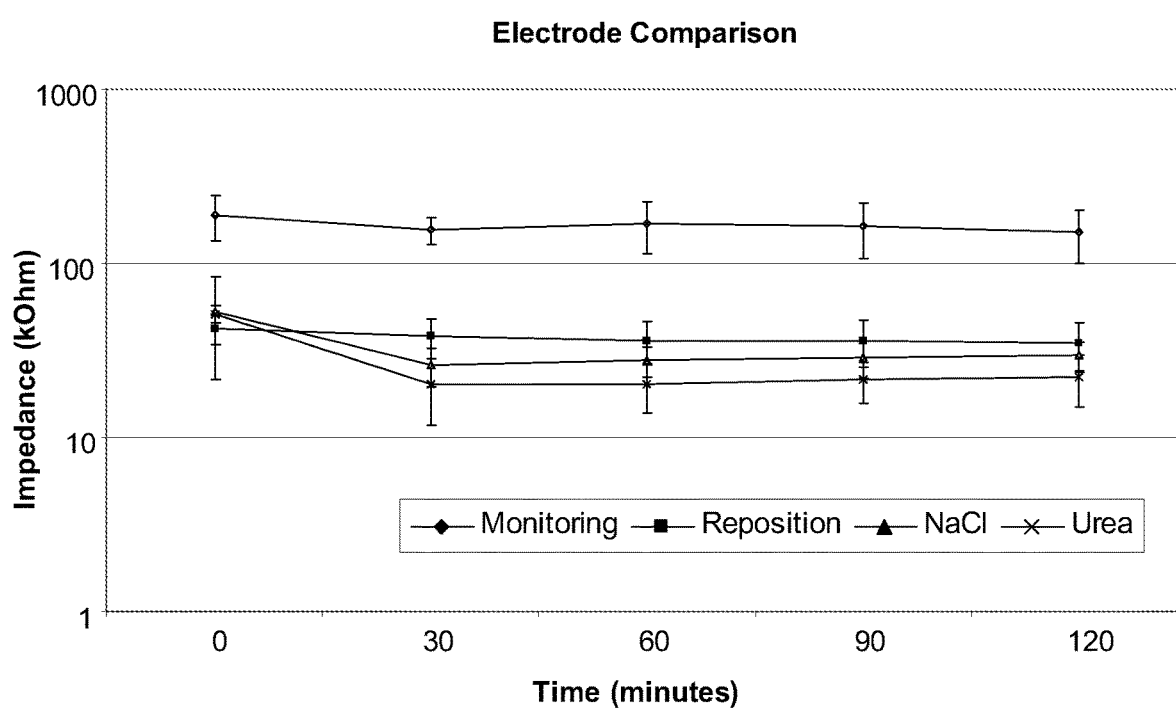
FIG. 13B illustrates a study of impedance as a function of time on a logarithmic scale for a commercially available 3M Red Dot 2760 Repositionable Monitoring Electrode, a commercially available 3M Red Dot 2570 Radiolucent Monitoring Electrode, a polyacrylate electrode of the present invention without urea in the absorbed electrolyte fluid and a polyacrylate electrode of the present invention with urea in the absorbed electrolyte fluid, on human forearm without skin preparation, using two-point impedance spectroscopy.
Figure 13C:
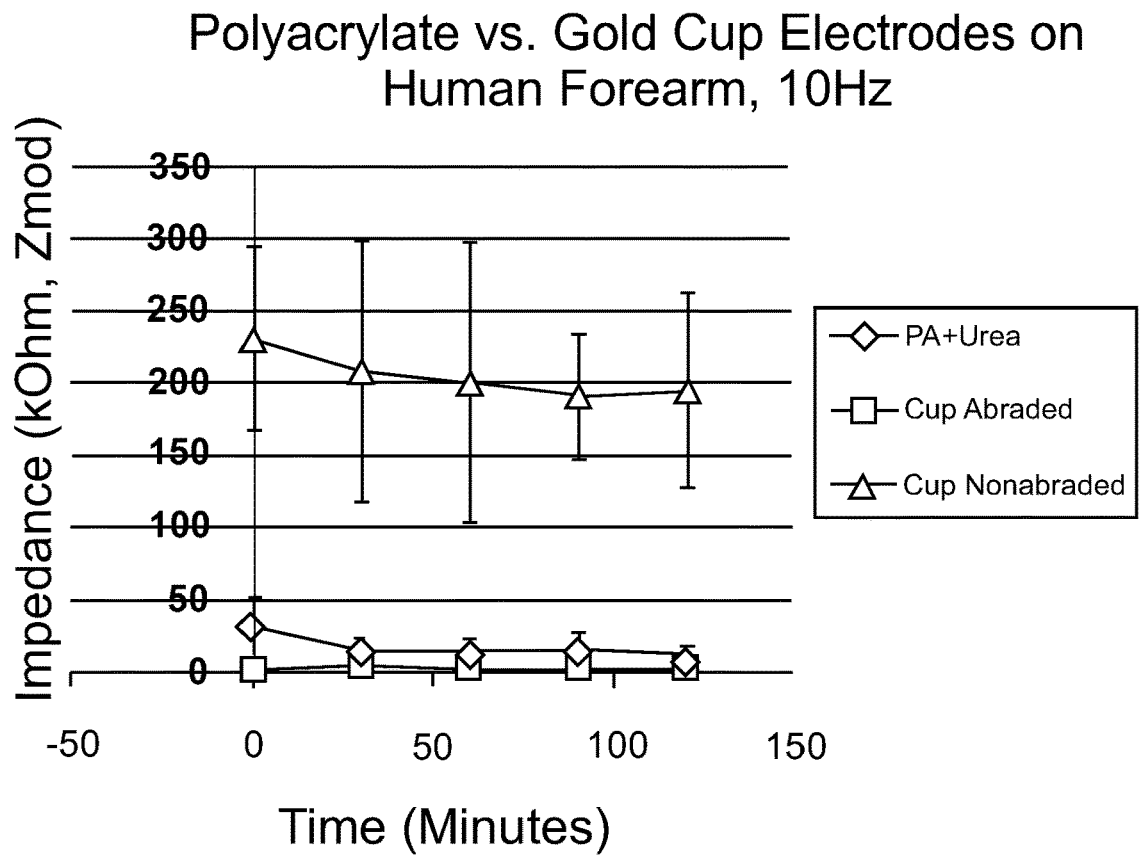
FIG. 13C illustrates a comparison of specific impedance of polyacrylate (sodium chloride+urea) electrodes of the present invention on non-prepared (non-abraded) skin with commercial gold-plated EEG disc electrodes (available from Chalgren Enterprises, Inc. of Gilroy, Calif.) coated with Ten20 conductive paste (available from Weaver and Co. of Aurora, Colo.) on both abraded and non-prepared skin.

FIG. 13A through 13C illustrate the results of several studies of the effect of urea as a penetration enhancer. Once again, in several studies, solutions were prepared containing either (i) 10.7% (w/w) sodium chloride or (ii) 9.1% (w/w) sodium chloride and 15% (w/w) urea. In several studies, subject skin was covered with a sponge soaked with the solutions and the skin was tested before and after the soak. The presence of urea in the solution reduced operating electrode impedance. In several other studies, skin was exposed to each solution as described above over time and impedance was measured as a function of time over several intervals of time. The presence of urea was found to reduce impedance at each time interval.

In a number of studies, data were collected from several individual subjects and forearm locations. In that regard, data were collected from several (for example, three, four or five) subjects, employing both forearms on each subject. In the studies, a small patch of skin on the inner forearm was well abraded with an abrasive surface. A Red Dot 2360 resting EKG electrode available from 3M was affixed to the abraded patch to act as a reference. The surrounding forearm skin was gently washed with liquid hand soap and patted dry to assure that all subjects presented uniform skin conditions and surface composition. After washing, the skin was allowed to dry for thirty minutes. After thirty minutes had passed, four prepared polyacrylate electrodes 310 (two swelled in sodium chloride and two swelled in sodium chloride plus urea, 0.1% crosslinker) were affixed to the inner forearm (without abrasion) using adhesive bandages. Electrodes 310 were positioned in an alternating fashion to assure varying locations for each electrode composition.

Impedance measurements were performed on each electrode 310 at the moment of application (time zero) and again at thirty minute intervals over the course of two hours. Measurements were performed using a Gamry FAS2 Femtostat in a potentiostatic EIS mode using a two-point method (in which the reference and counter leads were shorted together and affixed to the Red Dot reference electrode). Impedance data were collected from 1 to 10,000 Hz at 0V DC and 5 mV RMS. For comparison, six 3M Red Dot 2760 Repositionable Monitoring Electrodes and six 3M Red Dot 2570 Radiolucent Monitoring Electrodes as well as six conventional gold plated EEG disc electrodes (Chalgren Enterprises, Inc, Gilroy, Calif.) coated with Ten20 conductive paste (Weaver and Co., Aurora, Colo.) on both abraded and non-abraded skin. The results of several such studies are set forth in FIGS. 13A and 13C. In general, the electrodes of the present invention operated at least as well as the commercially available electrode even though the preparatory step of skin abrasion was not used in connection with the electrodes of the present invention.

Figure 13D:
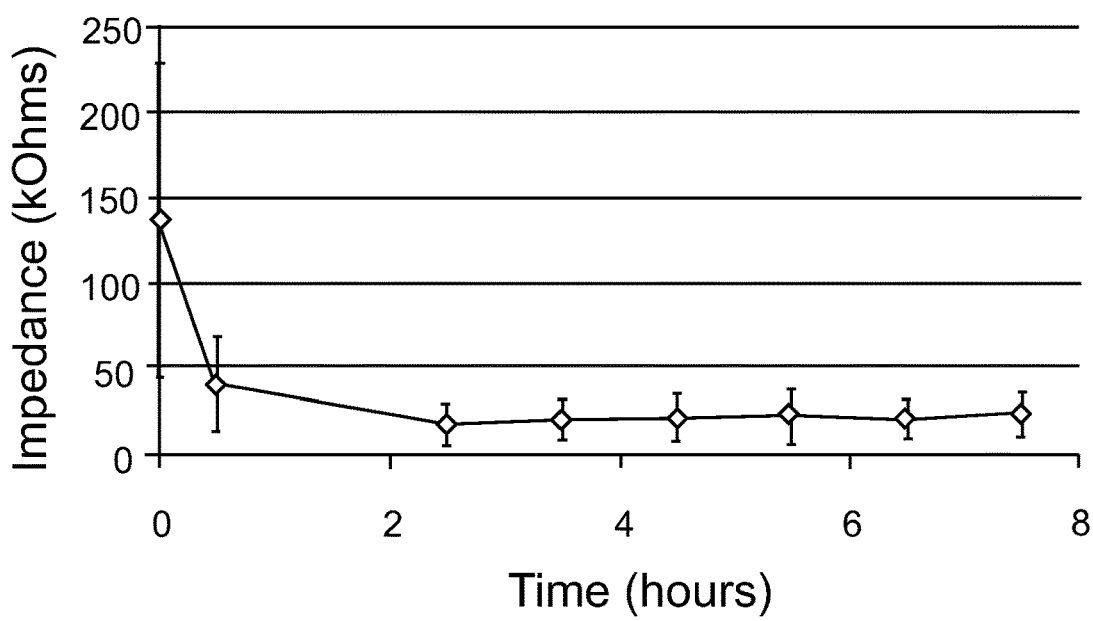
FIG. 13D illustrates a long-term study impedance as a function of time for a polyacrylate (sodium chloride+urea) electrode of the present invention on non-prepared (non-abraded) skin and commercial gold-plated EEG disc electrodes on both abraded and non-prepared skin.

Another experiment was conducted to assess performance of the electrodes over a longer period of time. Two prepared electrodes including 0.1% cross-linker synthesized polyacrylate were affixed to non-abraded skin on the left forearm of three different subjects. Impedance recording was performed using the same experimental setup as described above, with recordings being taken at one hour intervals over the course of seven and a half hours (the second recording was taken thirty minutes after time zero to assess impedance after the initial stabilization). The results of such studies are set forth in FIG. 13D. As illustrated, impedance remains relatively stable over an extended period of time.

Electroencephalography testing using electrodes of the present invention was performed using a Clevelabs BioRadio 150 system (Cleveland Medical Devices Inc, Cleveland, Ohio) coupled with a 64 channel electrocap system (Electro- Cap International Inc, Eaton, Ohio). Electrode placement was performed using two channels in differential mode, with one channel occupying the F3 scalp location and one channel occupying the F4 scalp location, using a standard international 10-20 placement scheme. Each channel was set up using an ipsilateral mastoid reference electrode and a common ground electrode on abraded elbow skin. For the purposes of studies of the present invention, the F3 electrode and associated reference electrode were prepared by placing a small piece of woven carbon fiber paper inside the electrocap cups against the metal base electrode to make the necessary connection, and filling the cups with polyacrylate powder paste (that is, a paste-like flowable material) swelled with 9.1% sodium chloride, 15% urea solution (w/w). The F4 electrode and associated reference electrode were prepared by filling the electrocap cups with Ten20 conductive EEG paste. All electrodes were secured to their respective scalp positions using gauze medical tape.

Figure 14:
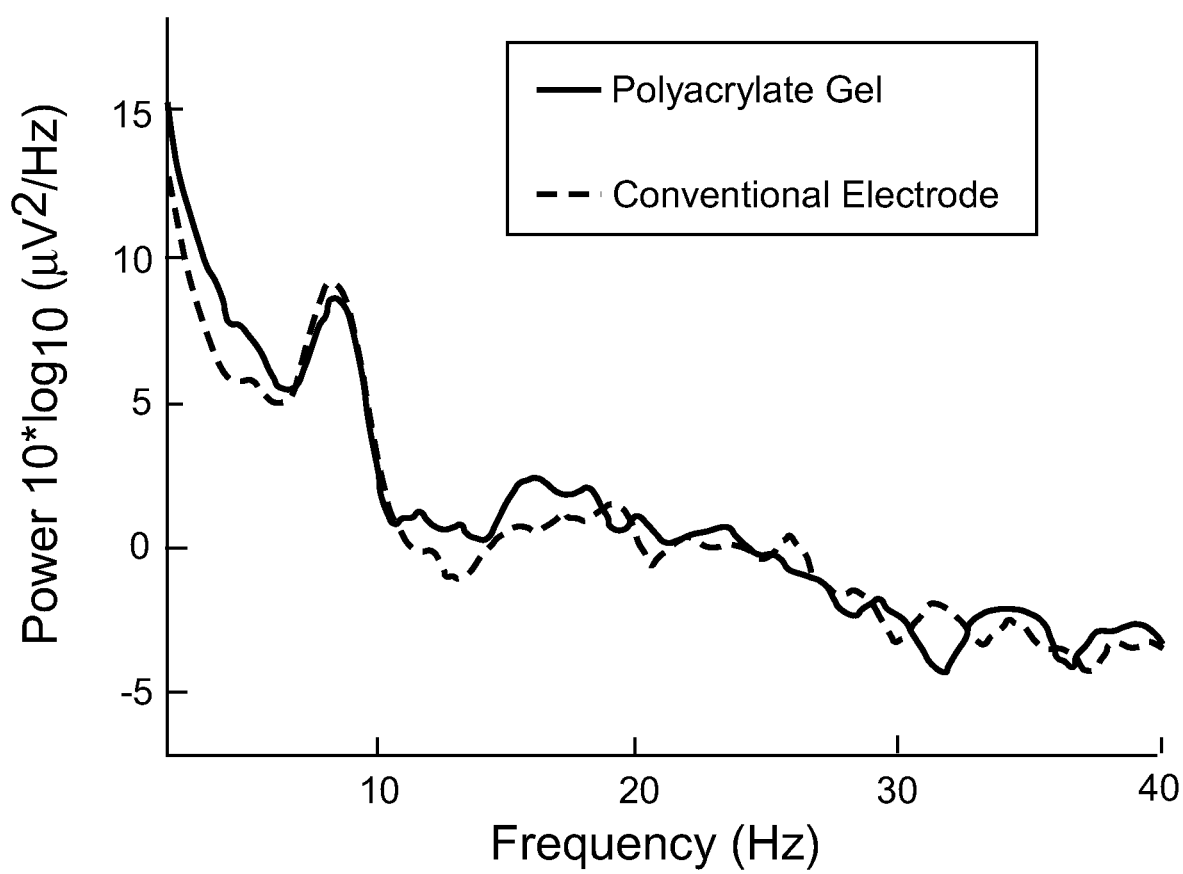
FIG. 14 illustrates time-frequency-topography or TFT analysis indicating frequency response of electrodes of the present invention and commercial gold-plated EEG disc electrodes using recorded resting EEG data.

EEG recording was performed for 60 seconds using a 480 Hz sampling rate and 12 bit resolution. A fourth-order DSP band-pass filter was applied to the instrument with low and high cut-off values of 1 and 45 Hz respectively. Data was recorded using Clevelabs BioRadio Capture Lite, and analyzed using the EEGlab 6.01b utility (UCSD Swartz Center for Computational Neuroscience, San Diego, Calif.) and Matlab 7.0.1. As illustrated, for example, in FIG. 14, hydrogel electrodes of the present invention captured frequency response features similar to conventional electrodes.

Evoked potentials were recorded using an EEG recording method coupled with an automated median nerve stimulation system. Three varieties of electrode systems (solid swelled cross-linked polyacrylate gel on non-prepared skin, swelled particulate polyacrylate flowable paste on non-prepared skin, and commercial cup EEG electrodes with Grass EC2 electrode cream and skin prepared and abraded using Nuprep abrasive gel) were studied. Polyacrylate electrodes were swollen using a 9.1% sodium chloride, 15% urea (w/w) aqueous solution. For recording, electrodes were situated at the F3 forehead location with an identical reference electrode placed on the ipsilateral mastoid. A counter electrode was situated at the Fz centroid location on well abraded skin. Recordings were taken from two subjects.

Recording was performed using a NeuroNet 650 intraoperative monitoring system using Neuro 6.0 software. Median nerve stimulation was performed using surface cup electrodes prepared with Nuprep ECG abrasive skin prepping gel and affixed using Grass EC2 electrode cream. Stimulation was performed at 3.43 Hz using a protocol developed by Computational Diagnostics, Inc. EEG recording was performed using a 3 kHz sampling rate.

To calculate signal to noise ratio for each electrode type, 500 recorded stimulation epochs were averaged together to compute an approximate signal tracing representative of the evoked potential for each stimulation trial. The noise of recording was estimated by subtracting the signal tracing from 500 epochs of raw recorded data. The power of the signal and noise tracings were computed and used to calculate the signal to noise ratio, using the formula 10 log 10 (signal power/noise power). Average SNR values across two subjects for solid cross-linked polyacrylate gel on non-abraded skin, polyacrylate flowable paste on non-abraded skin, and commercial EC2 paste on abraded skin were found to be −15.95 dB, −13.48 dB, and −12.59 dB respectively. Thus, the electrodes of the present invention compared well to the commercially available electrode, particularly considering the electrodes of the present invention were used in connection with non-abraded skin, whereas the commercially available electrode was used in connection with abraded skin.

Figure 9B:
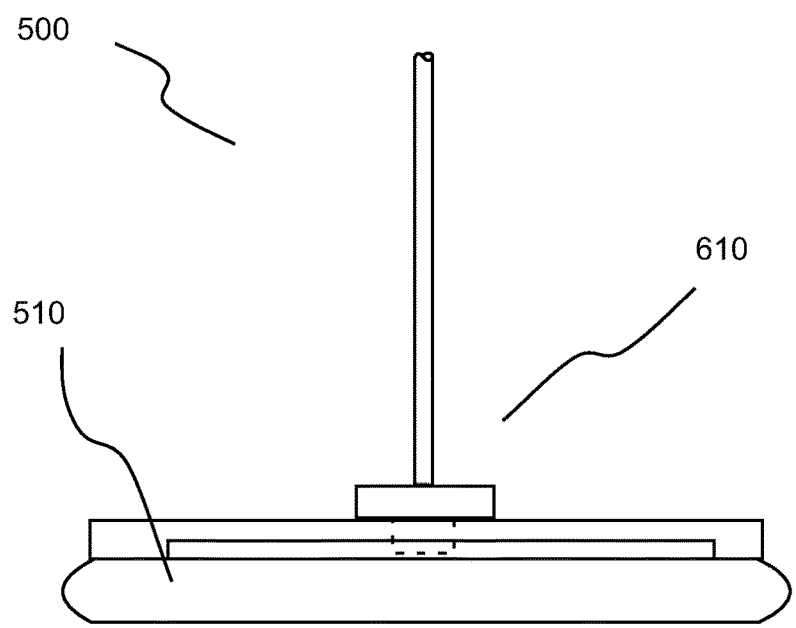
FIG. 9B illustrates an embodiment of an electrode system of the present invention in which a tissue contact element of the present invention is used in connection with a surface electrode, for example, in lieu of an electrolyte gel.

Although skin contact elements such as skin contact element 20 and 320 have been discussed in connection with incorporation thereof within tissue contact electrodes 10 and 310, respective, tissue contact elements of the present invention can be used in connection with various surface electrodes (including currently available surface electrodes) to, for example, maintain good ionic contact with the skin/tissue and/or maintain hydration thereof. FIG. 9B illustrates a surface electrode system 500 of the present invention in which a tissue contact element 510 of the present invention is used in connection with a surface electrode 610 (for example, a currently available surface electrode). Tissue contact elements 510 of the present invention can, for example, be used in lieu of an electrolyte gel. Unlike such electrolyte gels, tissue contact element 510 is a crosslinked gel and will not flow or spread under normal conditions. Moreover, tissue contact elements of the present invention provided improved water retention as compared to currently available electrolyte gels.

To assess the performance of the electrodes through dense human hair, an impedance experiment was performed on four different subjects. Skin behind an ear on each subject was well abraded using an abrasive pad, and a Red Dot 2670 repositionable monitoring electrode was applied to act as a counter electrode. A 0.1% cross-linker synthesized polyacrylate electrode was then pressed by hand against various locations on the subject's head, including the sideburn, the thin hair at the top of the forehead, and dense hair at the top of the scalp, along with a bare region of forehead to act as a control. After one minute had passed to allow for electrode stabilization, the impedance between the gel and counter electrode was measured using a Grass F-EZMS impedance meter (30 Hz). The impedance meter possesses a maximum limit of 200 kOhm.

Figure 15:
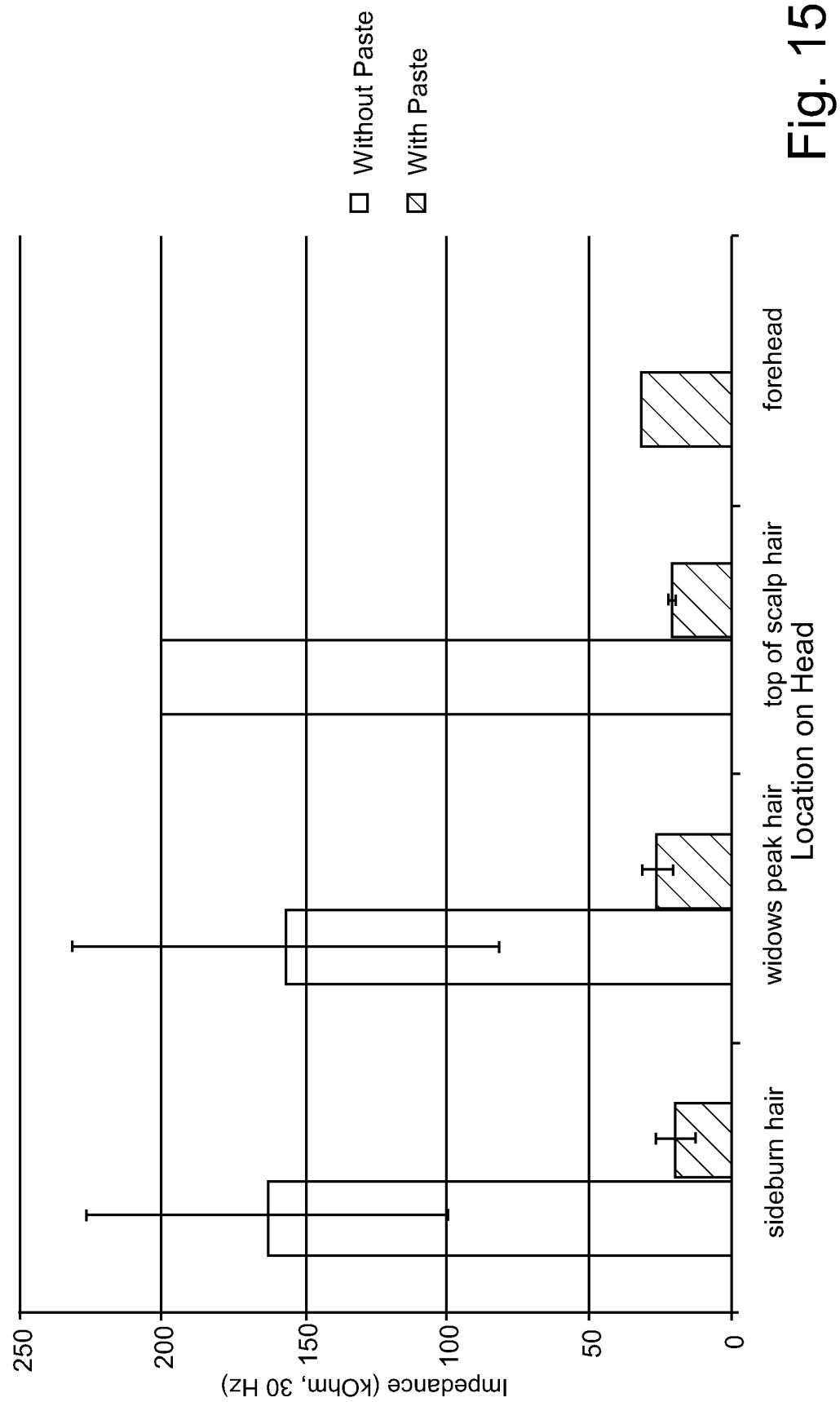
FIG. 15 illustrates a study of measured impedance of electrodes of the present invention on various locations on the head both with and without the use of a polyacrylate lower or intermediate contact element of the present invention in the form of a viscous flowable material or paste.

To evaluate whether or not a swelled particulate embodiment of the hydrogel would be more effective at penetrating the hair, pure polyacrylate powder (Flinn Scientific Inc, Batavia, Ill.) was soaked in the 9.1% sodium chloride, 15% urea solution (w/w). A lower or intermediate contact element including a pea-sized ball of the resulting mushy material was then pressed onto the scalp beneath the prepared polyacrylate electrode at each scalp location measured previously (see, for example, FIG. 18, which is discussed further below), and the impedance was recorded in an identical manner. As can be seen in FIG. 15, the lower or intermediate contact element/flowable paste was able to create an ionic pathway through the hair and significantly reduce the impedance to a range that is acceptable for EEG measurement.

As discussed briefly above, electrode surface polarization is an important concept that influences many aspects of electrochemical sensors. To convert an ionic current, such as a biopotential (where current is carried by diffusion of ionic species in solution) into an electric current in a metallic conductor (where current is carried by electron migration in a solid state material), a chemical reaction can take place at the surface of the electrode. This chemical reaction is typically in the form of metal atoms at the surface of the conductor giving up electrons and ionizing into the solution, or of metal ions in solution accepting electrons from the conductor and merging with the metal surface. Each atom that undergoes such a reaction process results in the transport of one electron of charge between the ionic current state and the electric current state, resulting in a faradic current across the interface.

The charge transport is dominated by the reaction kinetics of the material in question. Faradic current can only be transported as quickly and densely as the reaction kinetics allow. The reaction dynamics are typically a function of an activation energy and a reaction rate. In the case of very noble metals such as platinum, the rate of the reaction is very low as a result of the substantial stability of the material. In such situations, charges accumulate at the surface of the metal, with electrons accumulating within the bulk of the metal near the surface. Ionic species accumulate near the electrode in solution, but are unable to transfer as a result of the extremely slow rate of the corresponding surface reaction. A polarized interface is thus created as one side of the interface is predominantly positive and the other side is predominantly negative, essentially creating a capacitor at the surface electrode interface. This state allows capacitive current to flow through the junction only in the presence of a fluctuating potential. Thus, the higher the frequency, the lower the resistance, with resistance being at maximum at pure DC current. This state can provide significant sources of impedance to a system, particularly in low frequency applications such as measuring biopotentials (for example, in ECG).

Several techniques exist for reducing such dependence of impedance on frequency. As discussed above, polarization essentially results from the inability of the native chemical redox reaction at the electrode surface to keep up with the current required, which results in capacitance being the dominant charge transport mechanism. To minimize capacitive impedance and allow for a more direct faradic charge transport, it is often possible to modify the surface to introduce much more active chemical reaction mechanisms. For example, such a mechanism of operation occurs in the case of the silver/silver chloride (Ag/AgCl) electrode. Because the silver chloride salt ionizes nearly at equilibrium, silver chloride ionizes into silver ion and chloride ion and back again constantly and easily, with very little activation energy required. Thus, the introduction of the redox reaction pair allows charge transduction between the electrolyte solution and the silver to occur quickly enough that charge buildup and polarization never have a chance to occur, avoiding a substantial capacitive effect.

A second method of eliminating low frequency capacitive impedance is to change the dimensions or morphology of the surface. In this technique, charge transport is capacitive in nature as the noble chemical reaction remains unchanged. However, it is possible to take advantage of the fact that the entire exposed metal surface effectively acts as one big capacitor. As the capacitive properties are in part derived from the surface area, increasing the exposed surface area of the metal effectively increases the surface area of the capacitor, which has the effect of shifting the frequency dependence to lower frequencies. In other words, a larger surface area capacitor exhibits lower impedance than a lower surface area capacitor at the same frequency. Thus, it is possible to approximate non-polarizing electrode frequency-independent impedance behavior from a polarizing surface simply by maximizing the exposed surface area, and shifting the capacitive cut-off frequency below the region of interest. Increasing the surface area may have a number of additional effects on other involved mechanisms as well, and not simply on the change in capacitance.

In several embodiments of the present invention, conducting polymers are coated upon a conductive element to shift capacitive polarizing effects to frequencies lower than the frequency range of interest as described above. In one such embodiment, the conductive polymer PEDOT (described above) was coated upon a carbon electrode element. Although, carbon has been previously disclosed for use as an electrode element, bare carbon graphite is nearly inert in solution and has no reliable associated redox reaction. Thus, any charge transduction from solution to the conductive carbon or graphite will be nearly completely capacitive in nature. However, as it is one of the most inexpensive, convenient, and flexible non-metallic conductors available, it would be beneficial to use carbon for low-frequency, low-impedance electrode applications. While simply weaving a cloth out of carbon is an effective method of somewhat reducing low frequency impedance as a result of the increase in exposed surface area, such materials still exhibit substantial capacitive impedance (for example, approximately an order of magnitude at a frequency of 10 Hz).

The present inventors have discovered that coating materials with a conducting polymer such as PEDOT has the effect of significantly reducing low frequency impedance. Early tests were performed using bare platinum, which exhibits a very high degree of polarization. Remarkably, electropolymerizing a coating of PEDOT on the surface of a platinum electrode reduced the low frequency impedance to nearly that of an equivalent surface of silver chloride. On the basis of such promising results, similar studies were carried out with carbon paper. The exact mechanism involved in the impedance reduction by conductive polymers is not fully understood. Without limitation to any mechanism, it is possible that a conductive polymer coating (such as a PEDOT coating) increases the effective surface area through convolutions and porosity of the conductive polymer. While it is possible that the inherent redox reactions involved in associate of conductive polymers such as PEDOT with dopant molecules could allow for a chemical basis of charge transfer, this may have a potential dependence and could be complicated to evaluate.

In several studies, carbon fiber cloth was modified with conductive polymer. The carbon fiber cloth included approximately 50 micron diameter carbon fiber matted together at random fiber orientations. Woven carbon cloth and other forms of conductive carbon can also be used. Carbon fiber is often synthesized by the thermal pyrolysis of polymer fiber (typically polyacrylonitrile, though less expensive forms can be made from rayon or pitch). The temperature of the pyrolysis controls the final chemical nature of the carbon, with lower temperatures forming amorphous carbon strands and higher temperatures forming graphite.

In several studies of the present invention, a PEDOT coating was prepared as described below. A 0.1 M poly (styrene sulfonate), 0.01 M EDOT solution was prepared by combining 10.7 microliters EDOT and 183 mg PSS with 10 mL of DI water. Roughly 30-40 mL of solution was prepared using the above ratios. The solution was well stirred to ensure proper mixing of the components, as EDOT is not very soluble in water. The resultant solution was placed into a cell vial with an immersed platinum counter electrode. The cell vial was attached to the Gamry potentiostat for three-point chronoamperometry, using a calomel electrode as the reference. Carbon paper/cloth was shaped into a desired geometry, and the region to be coated was immersed in the solution and affixed to the working electrode of the potentiostat using platinum clips. PEDOT was electropolymerized by running a chronoamperometry sequence at 1.1V for 1200 seconds. The PSS serves as the dopant and counter-ion to the PEDOT, and also makes the polymerization bath conductive to allow for the reaction progression. The coated carbon paper/cloth was then removed, washed, and dried. Testing indicated that the new material exhibited low frequency impedance characteristics similar to those observed in silver chloride systems.

Figure 16A:
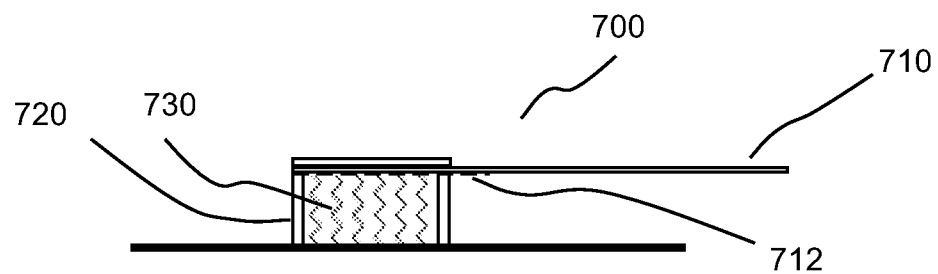
FIG. 16A illustrates a side cutaway view of another embodiment of an electrode system of the present invention including an electrode element including a conductive polymer.
Figure 16B:
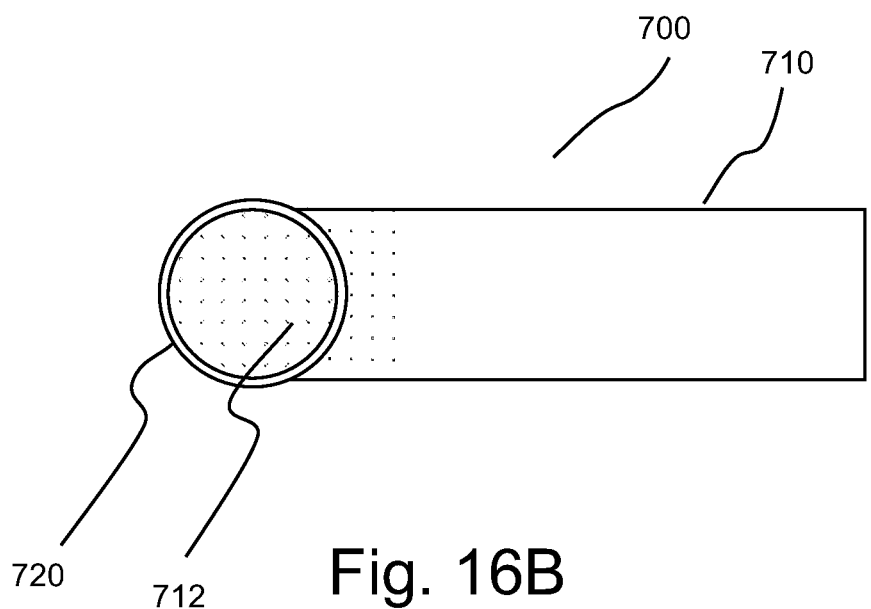
FIG. 16B illustrates a bottom view of the electrode system of FIG. 15A.

FIGS. 16A and 16B illustrate an embodiment of an electrode 700 of the present invention including a carbon electrode element 710 coated with a conductive polymer 712. The electrode include a well or seating 720 (for example, a cylindrical polymeric well) in which an electrode contact element 730 as described above is positioned in contact with electrode element 710.

FIG. 17A illustrates the results of a study of an electrode including PEDOT coated carbon electrode element as described above in 1×PBS (3-point EIS spectroscopy vs Calomel). In these studies, an uncoated stainless steel wire (0.5 mm diameter), a Ag/AgCl probe (0.8 mm diameter), an uncoated 6 mm*0.25 mm Toray carbon paper, and a PEDOT-coated 6 mm*0.25 mm Toray carbon paper were compared. The submersion depth was 6 mm. A carbon paper width of 6 mm corresponded to the approximate dimension of final backing sheet used in electrodes studied. The impedance values set forth are for a frequency of 10 Hz. FIG. 17B sets forth the data of FIG. 17A in an expanded scale to provide a more detailed comparison between the electrodes of the present invention and an Ag/AgCl electrode.

Figure 17C:
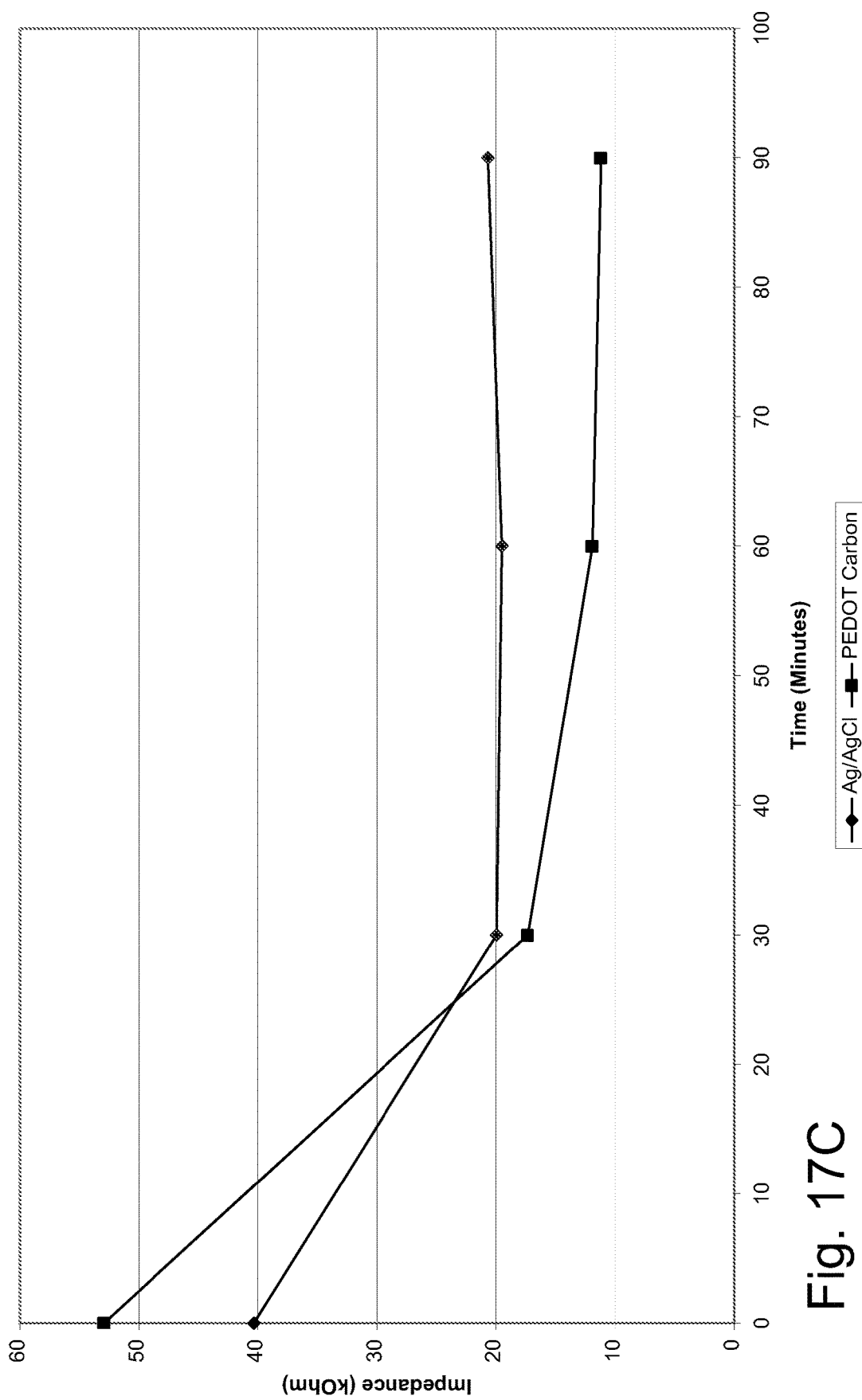
FIG. 17C illustrates a comparison of impedance on a human forearm as a function of time for an electrode including an Ag/AgCl electrode element and an electrode element including carbon coated with conducting polymer.

In the studies of FIG. 17C, a test similar to the forearm impedance tests performed with polyacrylate gel electrodes and Ag/AgCl electrodes was performed. In that regard, polyacrylate contact elements were swollen with an electrolyte solution including 10.7% NaCl and 15% Urea. The contact elements were pressed against inner human forearm skin with no surface preparation. The PEDOT-coated carbon paper electrode element was pressed on the other side of the contact element disk, and resultant electrodes were held in place by a BAND-AID® adhesive bandage. The loose end of the carbon paper was placed in electrical connection with the working electrode of a Gamry potentiostat. A well abraded 3M resting EKG electrode was used as the reference+counter. Measurements were taken at time 0 and then again at thirty minute intervals three times for a total of 90 minutes. FIG. 17C sets forth the data collected in this test for the electrodes of the present invention compared to the average data collected from 12 Ag/AgCl electrodes. As illustrated in FIG. 17C the electrodes of the present invention performed at least as well as the Ag/AgCl electrodes.

As used herein, the term "conductive polymers" refers generally to polymers which are conductive of electricity. Such polymers typically have a conjugated backbone with continuous overlapping orbitals. The extended delocalized bonds of conductive polymers provide charge mobility. As known in the art, for the polymer to be suitably electrically conductive, charge carriers are introduced by adding or removing electrons (normally achieved by oxidizing or reducing of the polymer). In several embodiments, conductive polymers used in forming electrode elements of the present invention are electrically polymerizable. Conductive polymers used in forming the electrodes elements of the present invention preferably exhibit a micro-morphology leading to increased interfacial area and facilitated charge transport. Suitable conductive polymers include, for example, polypyrrole, polythiophene, polyaniline and derivatives thereof.

In the representative embodiments described above, a conduct polymer was coated upon a conductive substrate or probe. However, the conductive polymers do not have to be a coating a carbon substrates. In that regard, the electrode element can be formed from the conductive polymer. For example, the electrode element can be formed from a film, sheet or other portion of the conductive polymer(s). A film of conductive polymer can, for example, be made by peeling the film off of a metallic substrate or synthesizing the film using a chemical reaction or by solution casting a polymer solution or suspension.

In several embodiments, smaller specific impedances of the electrodes of the present invention (as compared to currently available surface electrodes) enable the fabrication of electrodes of a smaller size than currently available, conventional electrodes such as those used in EEG and EKG studies. In several such embodiments, an elongated as opposed to flat design, as well as a tapered or pointed shape of the electrodes of the present invention allow application of the electrodes with minimal or no manual skin preparation. Such electrodes can readily replace commercially available or conventional electrodes.

In embodiments of the present invention including highly hydrated and non-tacky contact elements (as, for example, comprising crosslinked polyacrylate and similarly highly absorbent hydrogels) and/or intermediated contact element, the surface electrode systems of the present invention can provide improved hydration and impedance (particularly in performance in long-term studies) as compared to currently available surface electrode systems.

Further, the small size, high degree of hydration and/or deformability of the electrodes of the present invention can facilitate the use of electrodes of the present invention in arrays of many electrodes which can, for example, be integrated with an automated electrode placing system such as helmet 800 illustrated in FIG. 19. Skin preparation for sites covered with hair such as the head can be minimized. Moreover, tissue contact elements of the present invention can minimize or eliminate the requirement of skin abrasion.

Achieving an effective path for ionic conduction through dense scalp hair is a significant challenge toward the development of, for example, a next-generation EEG electrode. As discussed above, hair is typically simply parted, shaved, or otherwise physically removed from the system by the EEG operator, leaving the electrodes free to contact bare skin. However, the hair removal process is time consuming, especially in the case of multi-channel high resolution EEG when the preparation of over a hundred electrodes may be necessary. While moistening the hair with an electrolyte solution effectively penetrates the hair barrier and allows for effective ionic conduction, the system will dry out in a short period of time. The challenge is to develop a medium that will penetrate the hair effectively yet deliver enough electrolyte solution to the stratum corneum to enable effective preparation-free low impedance recording over long periods.

As discussed above, tissue contact elements of relatively small contact area can readily pass through hair to contact the skin. Such contact elements can be elongated to facilitate passage through hair. Highly hydrated, pliable or deformable contact elements can, for example, pass around hair to form good, wetted contact with skin.

Another effective option is to prepare a flowable variation of the polyacrylate-based (or other highly hydrated) hydrogel material of the present invention as discussed above. In several embodiments, flowable, paste-like materials were prepared by swelling powdered or particulate crosslinked polyacrylate with an electrolyte fluid. A flowable, paste-like material can also be formed from a non-flowable crosslinked matrix of a hydrogel such as polyacrylate by subjecting the matrix to sufficient mechanical perturbation (for example, mashing or smashing) to create a paste by breaking the crosslinked matrix. The flowable materials of the present invention exhibit Q and Q' values at least as high as the values set forth above for non-flowable, gel matrix contact elements. Indeed, Q and Q' values for the flowable materials can be even higher as additional electrolyte material can become trapped within or encapsulate by surrounding electrolyte-swollen particles. Preferably, an amount of electrolyte fluid is added so that the material is flowable (for example, under sufficient pressure), but can be formed into a shape without substantial running. In general, the morphology of the flowable materials can be similar to existing electrically conductive pastes and creams used, for example, in the EEG arts.

Swelling powdered or particulate crosslinked polyacrylate in, for example, 9.1% NaCl+15% Urea solution results in a mushy pasty hydrogel material which is flowable and malleable and moist to the touch. The highly hydrated flowable materials are not tacky. Studies (such as set forth in FIG. 15) have revealed that massaging a small amount of the electrolyte swelled polyacrylate flowable paste into the scalp hair before the application of a solid polyacrylate gel electrode of the present invention resulted in low impedance (for example, less than 20 kOhms) with no other surface preparation or skin abrasion necessary.

Without limitation to any mechanism, it is believed that the flowable paste penetrates the hair and creates an ionically conductive bridge between the gel electrode and the scalp beneath. The consistency, degree of adhesion, and resistance to drying of the paste could potentially be enhanced with a variety of additives while maintaining the benefits of the enormous swelling capacity and hydration potential of the polyacrylate gel principle component. The solid gel contact element and paste variations of the polyacrylate gel could be integrated with each other and designed into a unified electrode model, with the paste composing the lower skin-surface-contact element of the design.

Figure 18:
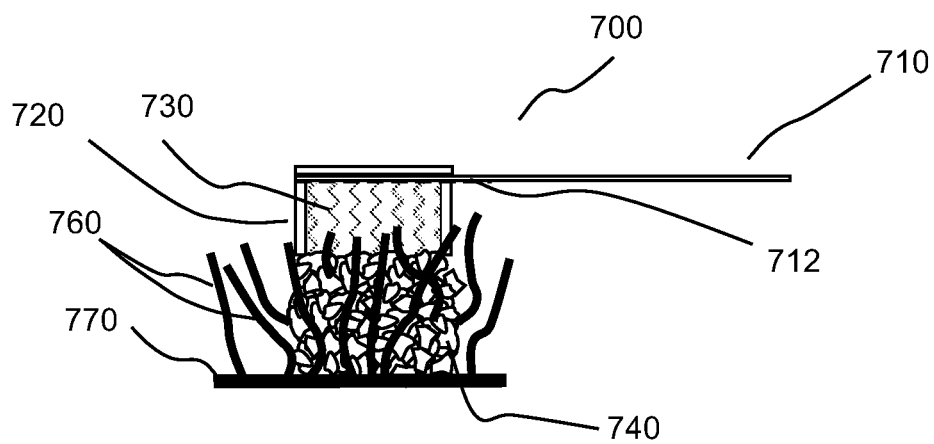
FIG. 18 illustrates the electrode system of FIG. 16A further including a lower or intermediate contact element including a swollen, particulate, crosslinked hydrophilic polymer, (for example, polyacrylate) that is flowable and adapted to pass through hair.

For example, FIG. 18 illustrates an idealized representation of electrode system 700 further including a lower or intermediate contact element 740, formed separately from electrode contact element 730 and including a flowable paste (for example, including individual particles of a hydrophilic polymer such as crosslinked polyacrylate swollen with NaCl and urea solution as described above), wherein lower or intermediate contact element 740 is penetrating or passing around hair 760 to provide wetted contact with skin 770.

Figure 19A:
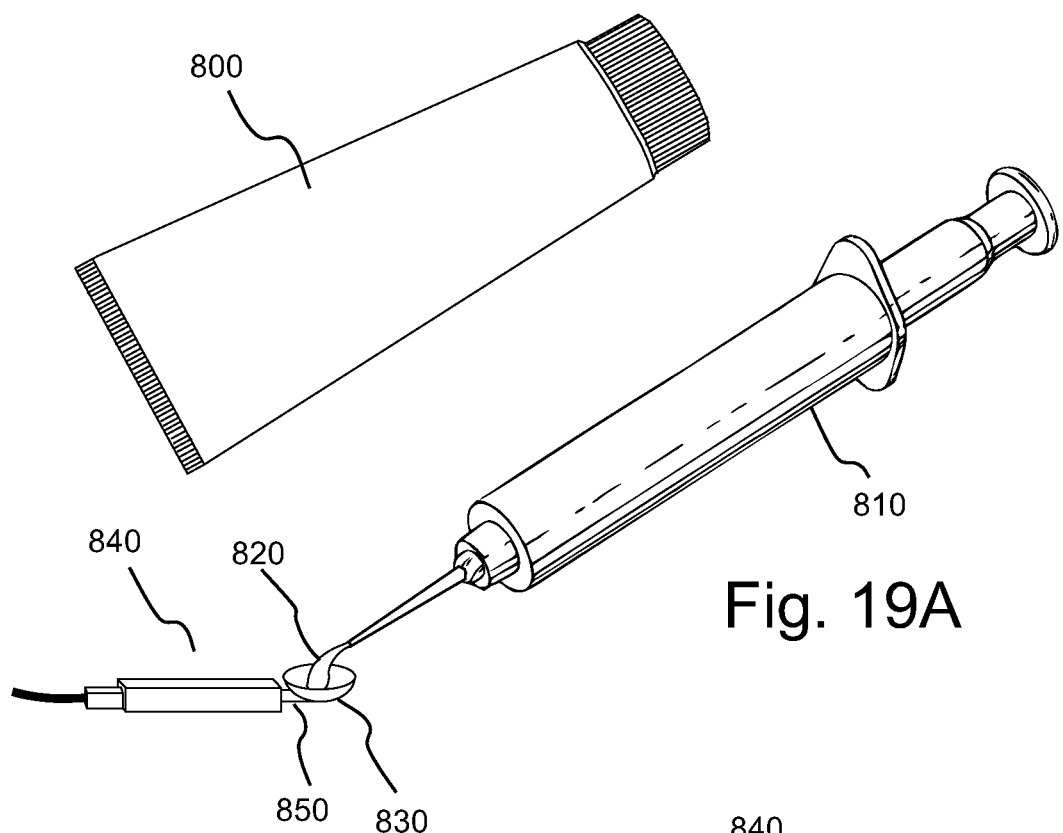
FIG. 19A illustrates the filling of a commercially available cup electrode with a flowable paste of the present invention to form a skin contact element.
Figure 19B:
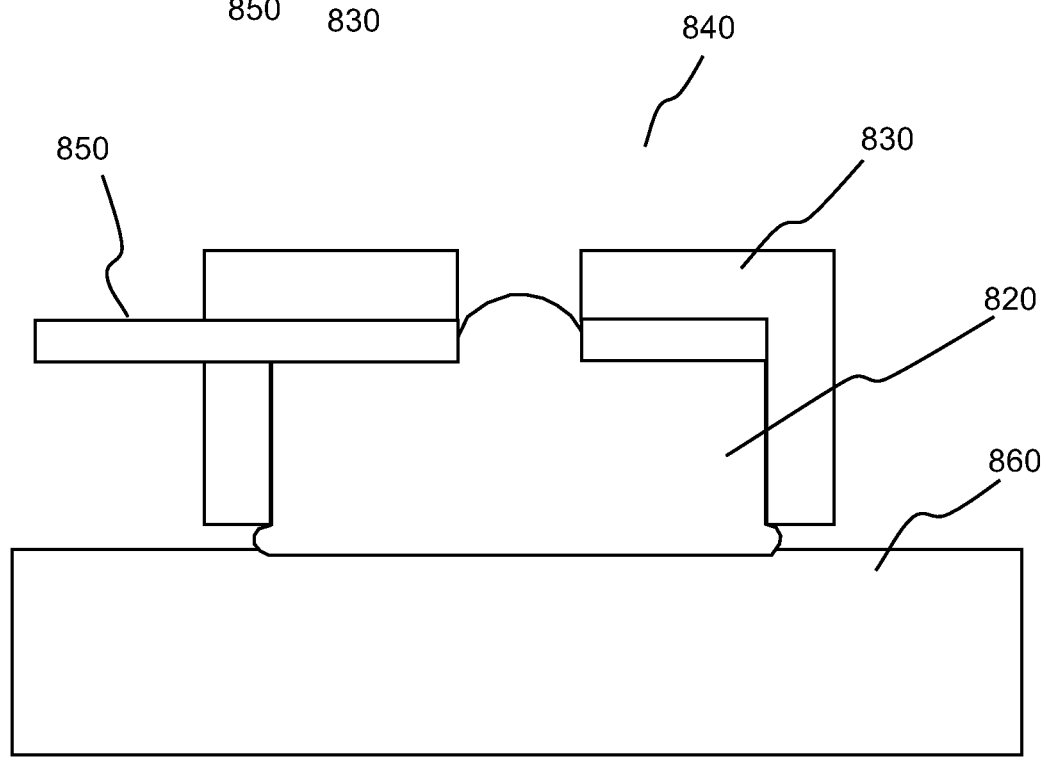
FIG. 19B illustrates an electrode including a commercially available cup electrode filled with a flowable paste of the present invention.

As described above, a flowable paste embodiment of an electrode material of the present invention can be prepared by swelling a powder or other particulate material wherein the individual particle are formed from a hydrophilic polymer (for example, a cross-linked polyacrylate) with electrolyte fluid/solution or by mechanically perturbing a cross-linked gel matrix until the desired consistency/flowability is achieved. Electrodes including a contact element including only the flowable paste material of the present invention (with no crosslinked solid gel element of the present invention) exhibit generally identical performance on non-prepared skin as do electrodes of the present invention including a solid, crosslinked gel contact element. The flowable and cohesive (which can also be (malleable or formable and moldable) materials of the present invention offer a number of benefits for a variety of applications. For example, the paste-like, flowable material is capable of readily traversing even dense scalp hair, with electrolyte-swollen particles penetrating between hair strands and creating a conductive bridge between the scalp and the electrodes of the present invention. Testing has indicated that the impedance of electrodes employed in this fashion over hair is effectively equivalent to the impedance of the same electrode over bare non-prepared skin. Additionally, the paste-like flowable materials of the present invention are compatible with any number of existing commercial EEG cup/holder electrodes or hairnet systems, and can be employed as a replacement for conventional electrode conductive creams and pastes. The paste-like material of the present invention can, for example, be easily stored and applied using a tube 800 or a syringe 810 as illustrated in FIG. 19A. FIG. 19A illustrates injection of paste-like material 820 from syringe 810 into a cup or holder 830 of an electrode 840. As known in the art, cup electrode 840 also includes an electrically conductive electrode lead 850. FIG. 19B illustrates a schematic representation of electrode 840 in contact with skin surface 860. The conductive, paste-like material of the present invention can thus be injected or squeezed from a tube into enclosed spaces using, for example, a large-bore needle or a squeeze tube. The paste can be employed as an intermediary material between a solid polyacrylate gel electrode element of the present invention (or another electrode element) and a surface such as skin. Alternatively, the flowable and cohesive paste-like material of the present invention can be use alone as the principal conductive contact material in an electrode or electrode system.

Figure 20:
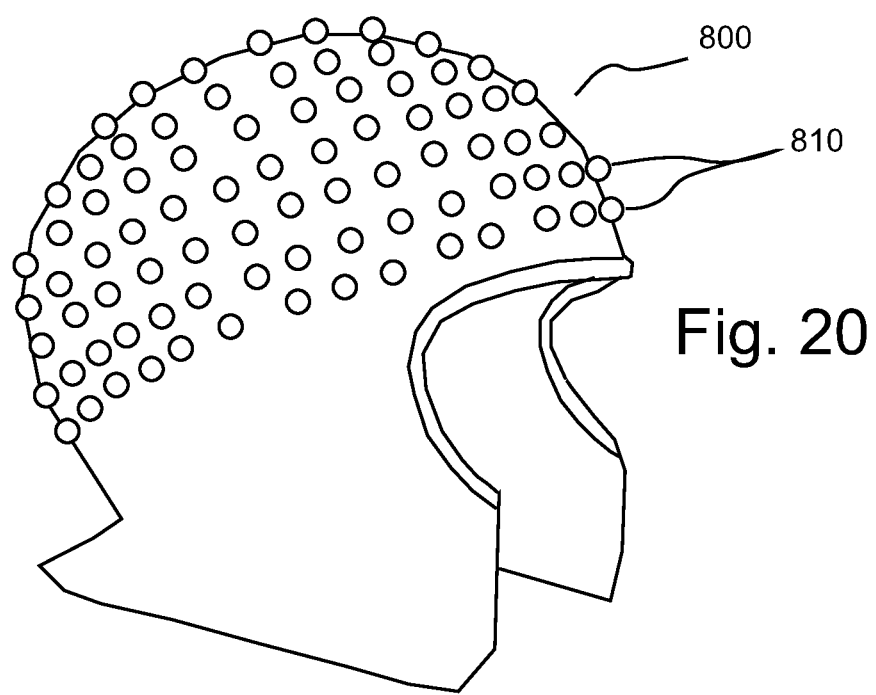
FIG. 20 illustrates an embodiment of an automated electrode placement system in which electrodes of the present invention can be incorporated.

An automated electrode placing system including an electrode system such as system 10, system 700 or system 840 can, for example, be used for multi-channel EEG recording. As illustrated, for example, schematically in FIG. 20, a system 900 or other application system or electrode system of the present invention can include biasing elements 910 (also see biasing element 110 in FIG. 1B) such as a spring-loaded element or other biasing element to maintain good connection between electrode systems 10 or electrode systems 700 and the skin surface.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method of measuring an electrical signal from living tissue comprising: placing a contact element in ionic contact with the tissue, the contact element comprising a crosslinked hydrophilic polymer matrix, such that the contact element has a Q' ratio of at least 5 as defined by the equation $$Q' = \frac{W_W}{W_G}$$

wherein $W_G$ is a dry weight of the crosslinked hydrophilic polymer and $W_W$ is weight of water in the sample after absorption of an electrolyte fluid comprising water and an electrolyte salt.

2. The method of claim 1 wherein the electrolyte fluid further comprises a penetration enhancer.

3. The method of claim 2 wherein the penetration enhancer comprises urea.

4. The method of claim 1 wherein the contact element is a component of an electrode system which further comprises a flowable and cohesive intermediate contact element, the cohesive intermediate contact element having a Q' ratio of at least 5.

5. The method of claim 4 wherein the cohesive intermediate contact element comprises individual particles of crosslinked hydrophilic polymer in which the electrolyte fluid comprising water and an electrolyte salt have been absorbed.

6. The method of claim 5 wherein the cohesive intermediate contact element has a Q' ratio of at least 6.

7. The method of claim 5 wherein the cohesive intermediate contact element has a Q' ratio of at least 7.

8. The method of claim 5 wherein the cohesive intermediate contact element has a Q' ratio of at least 10.

9. The method of claim 5 wherein the crosslinked hydrophilic polymer comprises polyacrylate or a derivative of polyacrylate.

10. The method of claim 9 wherein the polyacrylate is sodium polyacrylate, potassium polyacrylate or lithium polyacrylate.

11. The method of claim 5 wherein the electrolyte fluid further comprises a penetration enhancer.

12. The method of claim 11 wherein the penetration enhancer comprises urea.

13. The method of claim 1 wherein the contact element comprises a conductive polymer.

14. The method of claim 13 wherein the conductive polymer comprises at least one of polypyrrole, a derivative of polypyrrole, polythiophene, a derivative of polythiophene, polyaniline or a derivative of polyaniline.

15. The method of claim 13 wherein the conductive polymer comprises poly(3,4-ethylenedioxythiophene) or PEDOT.

16. The method of claim 13 wherein the contact element comprises individual particles of the crosslinked hydrophilic polymer.

17. The method of claim 1 wherein the contact element comprises a conductive substrate coated on at least a portion thereof with a conductive polymer.

* * * * *